(12) United States Patent
Tian et al.

(10) Patent No.: US 11,345,368 B2
(45) Date of Patent: May 31, 2022

(54) GUIDANCE SYSTEM, GUIDANCE METHOD, AND STORAGE MEDIUM

(71) Applicant: HONDA MOTOR CO., LTD., Tokyo (JP)

(72) Inventors: Lei Tian, Wako (JP); Masahiro Tada, Wako (JP)

(73) Assignee: HONDA MOTOR CO., LTD., Tokyo (JP)

( * ) Notice: Subject to any disclaimer, the term of this patent is extended or adjusted under 35 U.S.C. 154(b) by 156 days.

(21) Appl. No.: 16/744,329

(22) Filed: Jan. 16, 2020

(65) Prior Publication Data

US 2020/0231179 A1 Jul. 23, 2020

(30) Foreign Application Priority Data

Jan. 22, 2019 (JP) .............................. JP2019-008251

(51) Int. Cl.
| | |
|---|---|
| *A61B 5/18* | (2006.01) |
| *G07C 5/00* | (2006.01) |
| *B60R 11/02* | (2006.01) |
| *B60W 60/00* | (2020.01) |
| *G06T 11/60* | (2006.01) |
| *A61B 5/16* | (2006.01) |
| *G01C 21/36* | (2006.01) |
| *B60W 40/08* | (2012.01) |
| *G05D 1/02* | (2020.01) |

(52) U.S. Cl.
CPC ......... *B60W 60/0013* (2020.02); *A61B 5/165* (2013.01); *A61B 5/18* (2013.01); *B60W 40/08* (2013.01); *G01C 21/3667* (2013.01); *G05D 1/0212* (2013.01); *G06T 11/60* (2013.01); *G05D 2201/0212* (2013.01); *G05D 2201/0213* (2013.01)

(58) Field of Classification Search
CPC ...... A61B 5/18; G05D 1/0044; G05D 1/0027; G01C 21/3667; G07C 5/00; B60R 11/02
See application file for complete search history.

(56) References Cited

U.S. PATENT DOCUMENTS

| | | | |
|---|---|---|---|
| 10,268,191 B1 * | 4/2019 | Lockwood | ........... G05D 1/0027 |
| 10,564,638 B1 * | 2/2020 | Lockwood | ........... G05D 1/0044 |

FOREIGN PATENT DOCUMENTS

| | | | | |
|---|---|---|---|---|
| CN | 107358785 A | * | 11/2017 | ............... A61B 5/18 |
| JP | 2009123165 A | * | 6/2009 | ............. B60R 11/02 |
| JP | 2012113609 A | * | 6/2012 | ............... G07C 5/00 |
| JP | 2018-100936 | | 6/2018 | |
| JP | 2018100936 A | * | 6/2018 | ......... G01C 21/3667 |

* cited by examiner

*Primary Examiner* — Yuri Kan
(74) *Attorney, Agent, or Firm* — Amin, Turocy & Watson, LLP

(57) ABSTRACT

A guidance system includes an outputter configured to output information, a first acquirer configured to acquire position information indicating an occurrence position of a predetermined event that occurred due to at least the feelings of an occupant in a moving body, a second acquirer configured to acquire position information indicating a position of a first moving body, and an output controller that is configured to cause the outputter to output guidance information for providing guidance to the occupant in the first moving body regarding the fact that there is a possibility of the predetermined event occurring in the first moving body according to the position information acquired by the first acquirer and the position information acquired by the second acquirer.

15 Claims, 16 Drawing Sheets

| SPOT | PREDICTION MODEL |
|---|---|
| SP1 | MDL1 |
| SP2 | MDL2 |
| SP3 | MDL3 |
| ... | ... |

GUIDANCE SYSTEM, GUIDANCE METHOD, AND STORAGE MEDIUM

CROSS-REFERENCE TO RELATED APPLICATION

The present application claims priority based on Japanese Patent Application No. 2019-008251, filed on Jan. 22, 2019, the content of which is incorporated herein by reference.

BACKGROUND

Field of the Invention

The present invention relates to a guidance system, a guidance method, and a storage medium.

Description of Related Art

A technology in which a map on which information related to the feelings of an occupant in a vehicle is associated with position information of the vehicle is generated, and using the generated map, a route along which a vehicle that another occupant is in whose feelings and preferences are similar to a guidance target occupant has traveled in the past is selected from among a plurality of routes along which an unspecified large number of vehicles have traveled, and guidance along the selected route is performed for the guidance target occupant is known (for example, refer to Japanese Unexamined Patent Application, First Publication No. 2018-100936).

SUMMARY

However, in the conventional technology, an unexpected and unforeseen situation may occur on a route of which an occupant having boarded a moving body such as a vehicle has been informed.

The aspects of the present invention provide a guidance system, a guidance method, and a storage medium through which an occupant in a moving body is informed of a possibility of the occurrence of an unforeseen situation, and thus the occupant can be prepared for an unforeseen situation.

A guidance system, a guidance method, and a storage medium according to the present invention have the following configurations.

According to an aspect (1) of the present invention, there is provided a guidance system, including: an outputter which is provided in a first moving body and is configured to output information to the interior of the first moving body; a first acquirer configured to acquire position information indicating an occurrence position of a predetermined event that occurred due to at least the feelings of an occupant in a moving body; a second acquirer configured to acquire position information indicating a position of the first moving body; and an output controller that is configured to cause the outputter to output guidance information for providing guidance to the occupant in the first moving body regarding the fact that there is a possibility of the predetermined event occurring in the first moving body according to the position information acquired by the first acquirer and the position information acquired by the second acquirer.

According to an aspect (2), the guidance system of the aspect (1) further includes an estimator configured to estimate the feelings of the occupant in the first moving body, wherein the output controller is configured to cause the outputter to output the guidance information according to the position information acquired by the first acquirer, the position information acquired by the second acquirer, and the occupant's feelings estimated by the estimator.

According to an aspect (3), in the guidance system of the aspect (2), the outputter includes a display configured to display an image, and the output controller is configured to cause the display to display a map on which the position information acquired by the first acquirer is superimposed as the guidance information.

According to an aspect (4), the guidance system of the aspect (2) further includes a third acquirer configured to acquire path information indicating a first route along which the first moving body is scheduled to travel in the future, wherein the output controller is configured to cause the outputter to output information for prompting the occupant in the first moving body to change the first route to a second route on which the predetermined event is less likely to occur than on the first route according to the first route indicated by the route information acquired by the third acquirer, the position information acquired by the first acquirer, and the occupant's feelings estimated by the estimator as the guidance information.

According to an aspect (5), the guidance system of the aspect (2) further includes a route determiner configured to determine a first route along which the first moving body is scheduled to travel in the future, wherein the route determiner is configured to change the first route to a second route on which the predetermined event is less likely to occur than on the first route according to the first route determined by the route determiner, the position information acquired by the first acquirer, and the occupant's feelings estimated by the estimator.

According to an aspect (6), the guidance system of the aspect (2) further includes a driving controller configured to control a speed and steering of the first moving body; and a third acquirer configured to acquire route information indicating a first route along which the first moving body is scheduled to travel in the future, wherein the driving controller moves the first moving body from the first route to a second route on which the predetermined event is less likely to occur than on the first route according to the first route indicated by the route information acquired by the third acquirer, the position information acquired by the first acquirer, and the occupant's feelings estimated by the estimator.

According to an aspect (7), in the guidance system according to any one of the aspects (2) to (6), when the position of the first moving body indicated by the position information acquired by the second acquirer is on a route along which the moving body has traveled before it reaches a spot at which the predetermined event has occurred, and the occupant's feelings estimated by the estimator is included in a history of the feelings of the occupant in the moving body before it reaches a spot at which the predetermined event has occurred, the output controller is configured to cause the outputter to output the guidance information.

According to an aspect (8), the guidance system according to any one of the aspects (2) to (7) further includes a fourth acquirer configured to acquire speed information indicating a speed of the first moving body, wherein, when the position of the first moving body indicated by the position information acquired by the second acquirer is on a route along which the moving body has traveled before it reaches a spot at which the predetermined event has occurred, and the occupant's feelings estimated by the estimator is included in a history of the feelings of the occupant in the moving body before it reaches a spot at which the predetermined event has occurred, and additionally, the speed of the first moving body indicated by the speed information acquired by the fourth acquirer is included in a history of the speed of the moving body before it reaches a spot at which the predetermined event has occurred, the output controller is configured to cause the outputter to output the guidance information.

According to an aspect (9), in the guidance system according to any one of the aspects (2) to (8), when the position of the first moving body indicated by the position information acquired by the second acquirer is on a route along which the moving body has traveled before it reaches a spot at which the predetermined event has occurred, and the occupant's feelings estimated by the estimator is included in a history of the feelings of the occupant in the moving body before it reaches a spot at which the predetermined event has occurred, and additionally the weather when the occupant's feelings is estimated by the estimator is the same as the weather when the predetermined event has occurred, the output controller is configured to cause the outputter to output the guidance information.

According to an aspect (10), in the guidance system according to any one of the aspects (2) to (9), when the position of the first moving body indicated by the position information acquired by the second acquirer is on a route along which the moving body has traveled before it reaches a spot at which the predetermined event has occurred, and the occupant's feelings estimated by the estimator is included in a history of the feelings of the occupant in the moving body before it reaches a spot at which the predetermined event has occurred, and additionally, the time at which the occupant's feelings is estimated by the estimator is the same as the time at which the predetermined event has occurred, the output controller is configured to cause the outputter to output the guidance information.

According to an aspect (11), in the guidance system according to any one of the aspects (2) to (10), when the first moving body is present in a predetermined area in which feelings of occupants in a plurality of moving bodies that have caused the predetermined event have a predetermined tendency, and the feelings of the occupant in the first moving body estimated by the estimator has the predetermined tendency, the output controller is configured to cause the outputter to output the guidance information.

According to an aspect (12), in the guidance system according to any one of the aspects (1) to (11), the guidance information includes information for guiding, the occupant in the first moving body, to change the route of the first moving body or information for prompting to change the feelings.

According to another aspect (13) of the present invention, there is provided a guidance system, including: an outputter which is provided in a first moving body and is configured to output information to the interior of the first moving body; an acquirer configured to acquire position information indicating a position of the first moving body; an estimator configured to estimate feelings of an occupant in the first moving body; and an output controller that is configured to cause the outputter to output guidance information for providing guidance to the occupant in the first moving body the fact that there is a possibility of the predetermined event occurring in the first moving body according to output results of a model which is learned to predict that a predetermined event will occur when information including a position of a moving body and feelings of the occupant in the moving body is input, in which information including a position of the first moving body indicated by the position information acquired by the acquirer and the feelings of the occupant in the first moving body estimated by the estimator is input to the model.

According to another aspect (14) of the present invention, there is provided a guidance method causing a computer mounted in a first moving body including an outputter configured to output information to: acquire position information indicating an occurrence position of a predetermined event that occurred due to at least the feelings of an occupant in a moving body; acquire position information indicating a position of the first moving body; and cause the outputter to output guidance information for providing guidance to the occupant in the first moving body the fact that there is a possibility of the predetermined event occurring in the first moving body according to the position information indicating the occurrence position of the predetermined event and the position information indicating the position of the first moving body.

According to another aspect (15) of the present invention, there is provided a computer-readable storage medium storing a program causing a computer mounted in a first moving body including an outputter configured to output information to execute: acquiring position information indicating an occurrence position of a predetermined event that occurred due to at least the feelings of an occupant in a moving body; acquiring position information indicating a position of the first moving body; and causing the outputter to output guidance information for providing guidance to the occupant in the first moving body the fact that there is a possibility of the predetermined event occurring in the first moving body according to the position information indicating the occurrence position of the predetermined event and the position information indicating the position of the first moving body.

According to any one of the aspects (1) to (15), an occupant in a moving body is informed of a possibility of the occurrence of an unforeseen situation, and thus the occupant can be prepared for an unforeseen situation.

DESCRIPTION OF EMBODIMENTS

A guidance system, a guidance method, and a storage medium according to embodiments of the present invention will be described below with reference to the drawings.

First Embodiment

[System Configuration]

Figure 1:
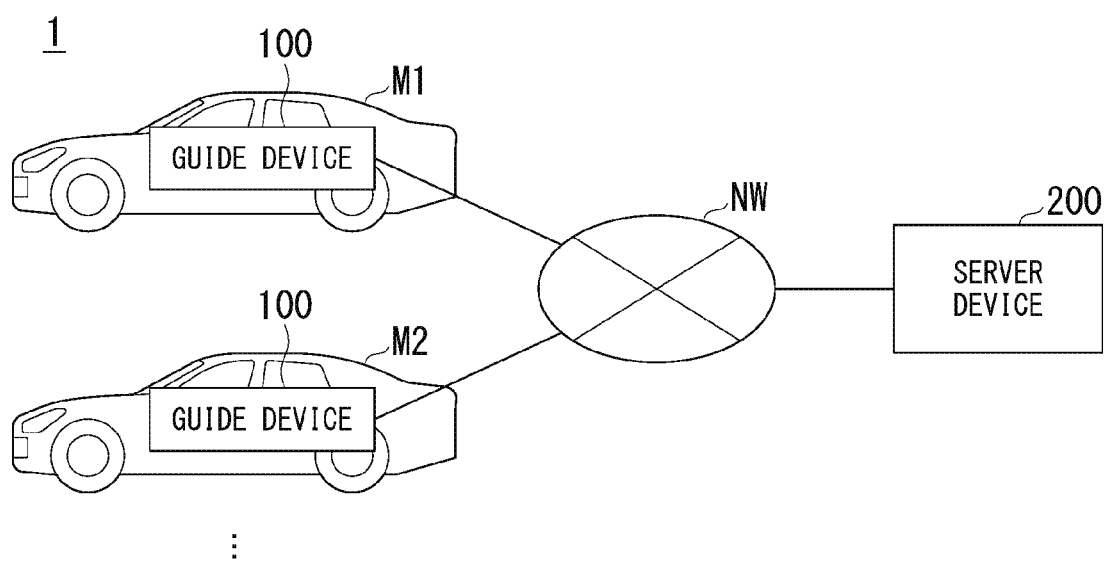
FIG. 1 is a diagram showing an example of a configuration of a guidance system according to a first embodiment.

FIG. 1 is a diagram showing an example of a configuration of a guidance system 1 according to a first embodiment. The guidance system 1 according to the first embodiment includes, for example, a plurality of guide devices 100, and a server device 200. As shown in the example in FIG. 1, each of the guide devices 100 is mounted in a vehicle M. The vehicle M is, for example, a vehicle with two wheels, three wheels, four wheels, or the like. A driving source of such a vehicle may be an internal combustion engine such as a diesel engine and a gasoline engine, an electric motor, or a combination thereof. The electric motor operates using electric power generated from a generator connected to an internal combustion engine or discharge electric power of a secondary battery or a fuel cell.

The guide device 100 and the server device 200 are communicably connected via a network NW. The network NW includes a local area network (LAN), a wide area network (WAN), and the like. The network NW may include, for example, a network using wireless communication such as Wi-Fi and Bluetooth (registered trademark, hereinafter omitted).

The guide device 100 is a device having functions of guiding an occupant in the vehicle M regarding a spot at which a predetermined event is likely to occur or a spot having a high probability of the occurrence of the predetermined event on or near a route along which the vehicle M is scheduled to travel for calling attention, and performing guidance to a route on which the predetermined event is less likely to occur. The predetermined event is, for example, an event (accident) that hinders the progress of the vehicle M such as a traffic accident and a traffic jam. Examples of a traffic accident considered as the predetermined event include contact with a pedestrian during turning right or left, entering an intersection against a red light, and contact with a preceding vehicle.

The server device 200 communicates with the guide device 100 mounted in each vehicle M and collects various types of data from the guide device 100. The server device 200 analyzes the collected data and thus predicts whether each vehicle passes through a spot at which the predetermined event is likely to occur. When a vehicle is predicted to pass through a spot at which the predetermined event is likely to occur, the server device 200 transmits information for calling attention to the guide device 100 mounted in the vehicle, or transmits information for prompting to change the route to another route on which the predetermined event is less likely to occur. Here, information that prompts paying attention and changing the route will be collectively referred to as "guidance information."

Here, a moving body in which the guide device 100 is mounted is not limited to the vehicle M, and may be another moving body, for example, an aircraft such as a passenger aircraft, an airship, and a helicopter, or a ship such as a passenger ship. Hereinafter, as an example, a moving body that is the vehicle M will be described.

[Sequence of Guidance System]

Figure 2:
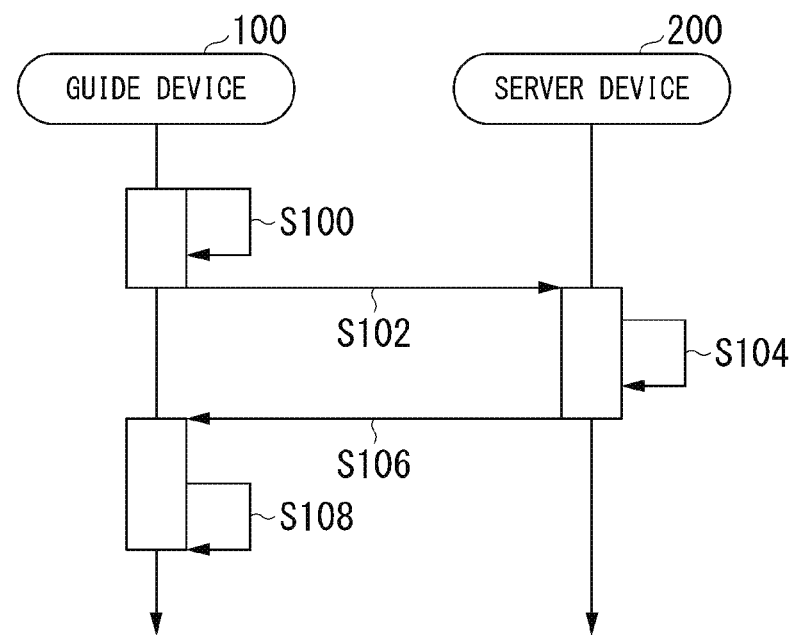
FIG. 2 is a sequence diagram showing a flow of a series of processes of the guidance system according to the first embodiment.

FIG. 2 is a sequence diagram showing a flow of a series of processes of the guidance system 1 according to the first embodiment. First, the guide device 100 collects driving data for an occupant in the vehicle M and profile data for the occupant (Step S100). The driving data is data including the situation inside the vehicle when an occupant drives the vehicle M, the status of the vehicle M, and the like, and more specifically, a vehicle type of the vehicle M, the weather during traveling, the time during traveling, the speed of the vehicle M, the number of passengers, the current position of the vehicle M, the location of the destination, the traveling route from the current position to the destination, the duration of driving of the occupant, whether there is conversation inside the vehicle M, an occupant's feeling, and the like are included. The profile data is data related to driving characteristics of an occupant and specifically includes an occupant's gender, age, and driving history, home location, residence area, driving tendencies, and the like. The driving tendency is, for example, a tendency to brake late when the duration of driving is long, a tendency to start suddenly when angry, or a tendency to forget to check side mirrors when talking with other occupants. When an accessory power supply and an ignition power supply of the vehicle M are turned on, the guide device 100 receives electric power supplied from these power supplies and is activated, and repeats collection of driving data at predetermined time intervals.

Next, the guide device 100 transmits the collected driving data and profile data to the server device 200 (Step S102).

When driving data and profile data are received from the guide device 100, the server device 200 predicts whether a vehicle that has transmitted the driving data and profile data passes through a spot at which the predetermined event is likely to occur based on the received driving data and profile data (Step S104).

When the vehicle is predicted to pass through a spot at which the predetermined event is likely to occur, the server device 200 transmits guidance information to the guide device 100 mounted in the vehicle (Step S106).

When guidance information is received from the server device 200, the guide device 100 prompts an occupant in the vehicle M to pay attention and change the route according to the guidance information (Step S108). Here, in this sequence, it is described that the guide device 100 that transmits information to the server device 200 in S102 and the vehicle in which the device is mounted are the same as the guide device 100 that receives information from the server device 200 in S106 and the vehicle in which the device is mounted, but transmission and reception may be performed by separate guide devices 100 and vehicles. That is, the guide device 100 that performs only transmission and the vehicle or the guide device 100 that performs only reception and the vehicle may be used.

[Configuration of Guide Device]

Figure 3:
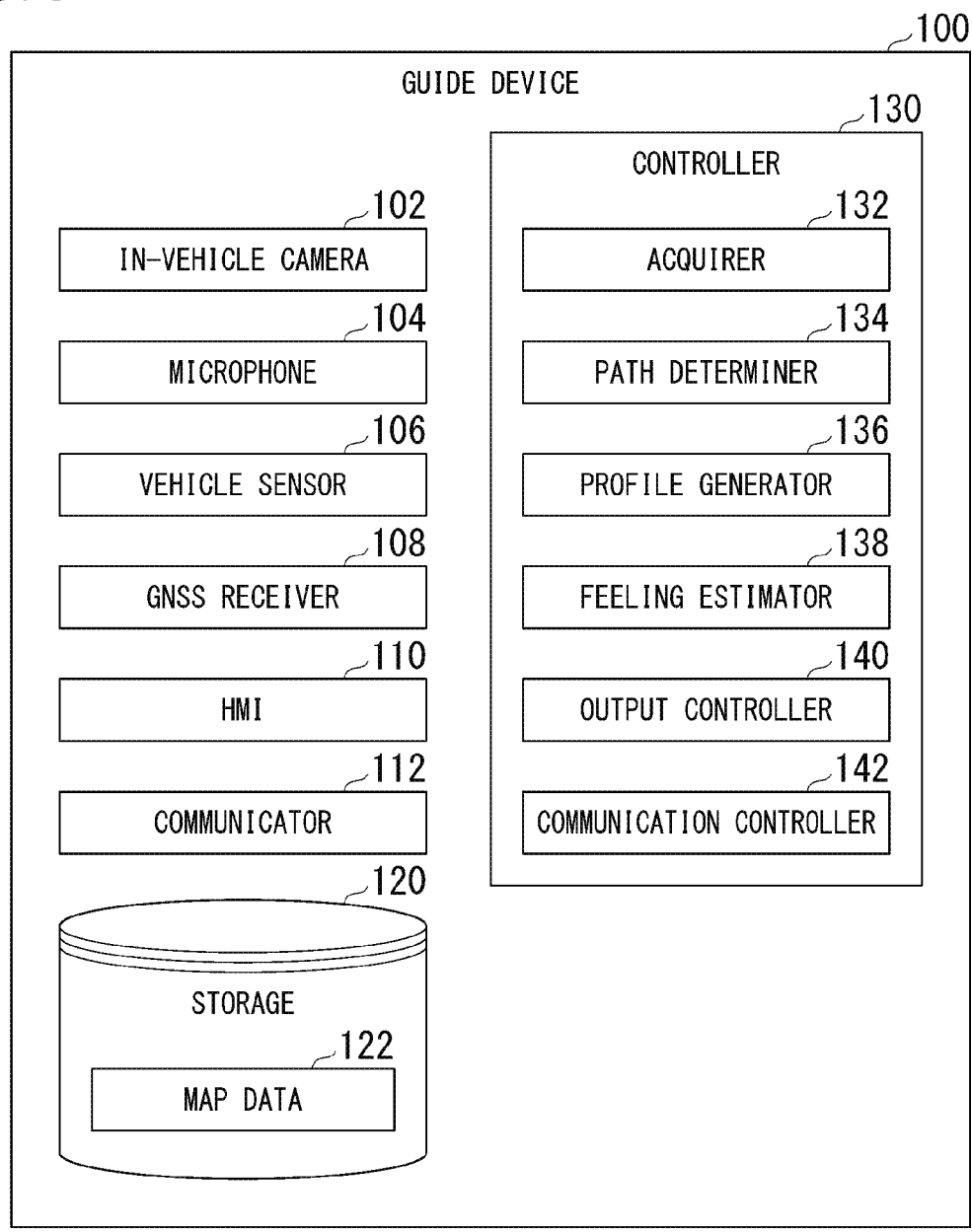
FIG. 3 is a diagram showing an example of a configuration of a guide device according to the first embodiment.

FIG. 3 is a diagram showing an example of a configuration of the guide device 100 according to the first embodiment. For example, the guide device 100 according to the first embodiment includes an in-vehicle camera 102, a microphone 104, a vehicle sensor 106, a global navigation satellite system (GNSS) receiver 108, a human machine interface (HMI) 110, a communicator 112, a storage 120, and a controller 130. These devices and instruments may be connected to one another via a multiplex communication line such as a controller area network (CAN) communication line, a serial communication line, a wireless communication network or the like. The configuration of the guide device 100 shown in FIG. 3 is only an example, and a part of the configuration may be omitted or other components may be additionally added.

For example, the in-vehicle camera 102 is installed in a cabin of the vehicle M in which the guide device 100 is mounted (hereinafter referred to as a host vehicle M) and images faces of occupants seated on seats in the cabin. The in-vehicle camera 102 is, for example, a digital camera using a solid-state image sensing device such as a charge coupled device (CCD) and a complementary metal oxide semiconductor (CMOS). For example, the in-vehicle camera 102 repeatedly images occupants at predetermined times. The in-vehicle camera 102 generates image data of imaged occupants and outputs the generated image data to the controller 130.

The microphone 104 is a sound input device that collects sound in the cabin of the host vehicle M. The microphone 104 outputs the collected sound data to the controller 130.

The vehicle sensor 106 includes a direction sensor configured to detect a direction of the host vehicle M, a vehicle speed sensor configured to detect a speed of the host vehicle M, an acceleration sensor configured to detect an acceleration of the host vehicle M, a yaw rate sensor configured to detect an angular velocity around the vertical axis of the host vehicle M, a torque sensor configured to detect a steering torque applied to rotating shafts of steering wheels, and the like. The vehicle sensor 106 outputs data including the detected orientation, speed, acceleration, and the like (hereinafter referred to as vehicle status data) to the controller 130.

The GNSS receiver 108 receives signals (radio waves) from satellites of Global Positioning System (GPS) and the like and specifies the position of the host vehicle M based on the received signals. The position of the host vehicle M may be specified or supplemented by an inertial navigation system (INS) using vehicle status data output from the vehicle sensor 106. The GNSS receiver 108 outputs position data indicating the specified position of the host vehicle to the controller 130.

The HMI 110 presents various types of information to an occupant in the host vehicle M and receives an operation input by the occupant. The HMI 110 includes a display, a speaker, a buzzer, a touch panel, a switch, a key, and the like. The HMI 110 is an example of "outputter."

The communicator 112 includes a communication interface, for example, an antenna and a network interface card (NIC). The communicator 112 communicates with the server device 200 via the network NW.

The storage 120 is realized by, for example, an HDD, a flash memory, an electrically erasable programmable read only memory (EEPROM), a read only memory (ROM), or a random access memory (RAM). In the storage 120, for example, map data 122 and the like are stored in addition to a program referred to by a processor to be described below. In addition, the map data 122 may be temporarily acquired from an external device (for example, the server device 200) and stored in the storage 120.

The map data 122 is, for example, data in which a road pattern is expressed with links indicating roads and nodes connected by links. The map data 122 may include road curvature and point of interest (POI) information and the like.

For example, the controller 130 includes an acquirer 132, a route determiner 134, a profile generator 136, a feeling estimator 138, an output controller 140, and a communication controller 142. These components are realized, for example, when a processor such as a central processing unit (CPU) and a graphics processing unit (GPU) executes a program (software). In addition, some or all of these components may be realized by hardware (circuit unit; including a circuitry) such as a large scale integration (LSI), an application specific integrated circuit (ASIC), and a field-programmable gate array (FPGA), or may be realized in cooperation of software and hardware. The program may be stored in the storage 120 in advance or may be stored in a removable storage medium such as a DVD and a CD-ROM, and may be installed in the storage 120 when the storage medium is mounted in a drive device.

The acquirer 132 acquires image data from the in-vehicle camera 102, acquires sound data from the microphone 104, acquires vehicle status data from the vehicle sensor 106, and acquires position data from the GNSS receiver 108. In addition, the acquirer 132 may acquire input data input to the HMI 110 by an occupant from the HMI 110. The input data includes, for example, destination position data. The acquirer 132 configured to acquire position data from the GNSS receiver 108 is an example of "second acquirer." In addition, the acquirer 132 configured to acquire vehicle status data from the vehicle sensor 106 is an example of "fourth acquirer."

For example, the route determiner 134 refers to the map data 122, and determines a route from the position the host vehicle M specified by the GNSS receiver 108 or an arbitrary position input to the HMI 110 by an occupant to the destination input to the HMI 110 by the occupant. The route determined by the route determiner 134 is an example of "first route." In addition, the route determiner 134 is an example of "third acquirer."

The profile generator 136 generates profile data based on various types of data acquired by the acquirer 132. The profile data is data related to driving characteristics of a person who can drive the host vehicle M such as an owner of the host vehicle M or a family of the owner.

For example, when an occupant inputs the gender, age, driving history, home location, residence area, and driving tendency to the HMI 110, the profile generator 136 may generate profile data based on the input data input to the HMI 110. In addition, the profile generator 136 may derive the home location and residence area based on the position data, derive the gender based on the image data and sound data, and derive the general driving tendency based on the vehicle status data and may generate profile data. When the profile generator 136 generates profile data, it stores the data in the storage 120.

Here, profile data may not be generated by the profile generator 136. For example, when profile data including the occupant's gender, age, driving history, home location, residence area, and driving tendency is input to a terminal device such as a smartphone that the occupant holds, the acquirer 132 may receive the profile data from the terminal device via the communicator 112. In addition, when profile data associated with an account for an application used in a terminal device is stored in an external device (for example, a server) and a user who uses the terminal device activates the application and authenticates the account, the acquirer 132 may acquire profile data of the user whose account is authenticated from the external device.

The feeling estimator 138 estimates the feelings of the occupant (in particular, a driver) boarded in the host vehicle M based on at least one or both of the sound data and image data acquired by the acquirer 132.

For example, the feeling estimator 138 extracts a period in which an occupant speaks (hereinafter referred to as a speech period) from the sound data acquired by the acquirer 132, converts sound for each extracted speech period into text, and thus generates text data indicating speech content. Then, the feeling estimator 138 estimates the feelings of the occupant based on the generated text data.

Specifically, the feeling estimator 138 inputs sound signals for each extracted speech period to a recurrent neural network including a bi-directional long short-term memory (BiLSTM) and an attention mechanism so that the sound signals are separated into a plurality of frequency bands such as a low frequency and high frequency bands and a spectrogram (Mel spectrogram) in which the sound signals in each frequency band are Fourier-transformed is obtained. The recurrent neural network may be learned in advance, for example, using training data in which sound signals for learning are associated as training labels with respect to a spectrogram generated from sound for learning.

When sound signals are converted into a spectrogram, the feeling estimator 138 inputs the spectrogram to a convolutional neural network including a plurality of hidden layers and thus obtains a string from the spectrogram. The convolutional neural network may be learned in advance, for example, using training data in which strings corresponding to sound signals used to generate the spectrogram for learning are associated as training labels with respect to the spectrogram for learning. The feeling estimator 138 generates string data obtained from the convolutional neural network as text data.

When text data is generated, the feeling estimator 138 inputs the generated text data to a deep neural network that is learned in advance so that the feelings of the occupant are analyzed, and thus an index that quantifies the feelings of the occupant (hereinafter referred to as a feeling index) is derived. In the feeling index, for example, a score indicating a likelihood of the feeling is associated with each parameter of various feelings such as anger, unpleasantness, fear, happiness, sadness, and surprise. Then, the feeling estimator 138 estimates the feelings of the occupant based on the derived feeling index.

In addition, the feeling estimator 138 may extract features of the occupant's face (for example, eyes, mouth, nose, and eyebrows) from the image data acquired by the acquirer 132 and estimate the feelings of the occupant based on the extracted face features. In addition, the feeling estimator 138 may recognize a gesture of the occupant from the image data and estimate the feelings of the occupant based on the recognized gesture.

In addition, the feeling estimator 138 may integrate the occupant's feeling estimation result using the sound data and the occupant's feeling estimation result using the image data and estimate the feelings of the occupant based on the integrated feeling estimation result.

The output controller 140 causes a display of the HMI 110 to display a route determined by the route determiner 134 on a map indicated by the map data 122 and thus guides a route from the current position to the destination for the occupant in the host vehicle M. In addition, when the communicator 112 receives guidance information from the server device 200, the output controller 140 causes the HMI 110 to output information for prompting the occupant to pay attention and information for prompting to change the route as an image or sound according to the guidance information.

The communication controller 142 controls the communicator 112, and transmits a combination of some or all of the image data, sound data, vehicle status data, position data, and input data acquired by the acquirer 132 and data indicating the occupant's feeling estimated by the feeling estimator 138 (hereinafter referred to as feeling estimation data) to the server device 200 as driving data. In addition, the communication controller 142 controls the communicator 112 and transmits the profile data generated by the profile generator 136 and the profile data acquired by the acquirer 132 to the server device 200.

[Processing Flow of Guide Device]

Figure 4:
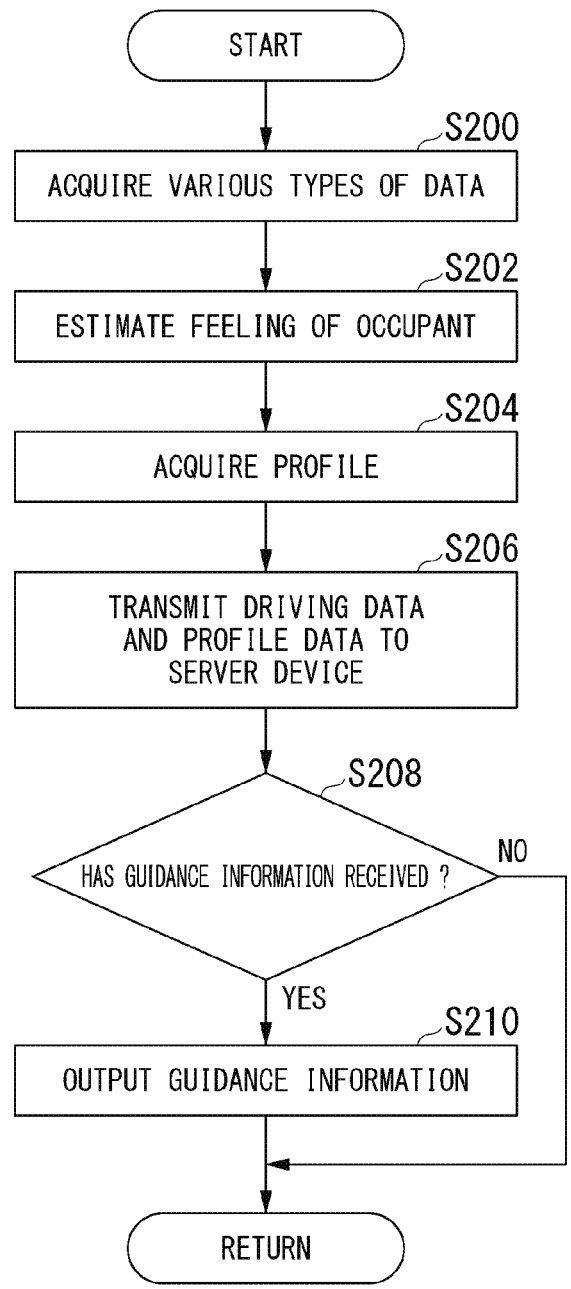
FIG. 4 is a flowchart showing a flow of a series of processes of the guide device according to the first embodiment.

Processes of the guide device 100 according to the first embodiment will be described below with reference to a flowchart. FIG. 4 is a flowchart showing a flow of a series of processes of the guide device 100 according to the first embodiment. The processes of this flowchart may be repeated at predetermined time intervals, for example, while an accessory power supply and an ignition power supply of the host vehicle M are turned on and the guide device 100 receives supply of electric power from these power supplies.

First, the acquirer 132 acquires various types of data such as image data, sound data, vehicle status data, position data, and input data (Step S200).

Next, the feeling estimator 138 estimates the feelings of the occupant in the host vehicle M based on at least one of the image data and sound data acquired by the acquirer 132 (Step S202).

Next, the profile generator 136 acquires profile data generated at another time from the storage 120 (Step S204). For example, the profile generator 136 generates profile data using a period different from the processing period of this flowchart and stores the data in the storage 120, and acquires profile data from the storage 120 according to the processing cycle of S204 in this flowchart. Here, the profile generator 136 may generate profile data at a time of the process in S204 in place of acquiring profile data generated in advance from the storage 120.

Next, the communication controller 142 transmits driving data including the data acquired by the acquirer 132 in the process of S200 and feeling estimation data indicating the occupant's feeling estimated by the feeling estimator 138 in the process of S202 and the profile data acquired or generated by the profile generator 136 in the process of S204 to the server device 200 via the communicator 112 (Step S206).

Next, from when the driving data and the profile data are transmitted to the server device 200 until a predetermined time has elapsed or until a predetermined distance is traveled, the communication controller 142 determines whether the communicator 112 has received guidance information from the server device 200 (Step S208).

When the communicator 112 has received guidance information from the server device 200, the communication controller 142 causes the HMI 110 to output the guidance information (Step S210). Thereby, the process of this flowchart ends.

[Configuration of Server Device]

Figures 5, 6:
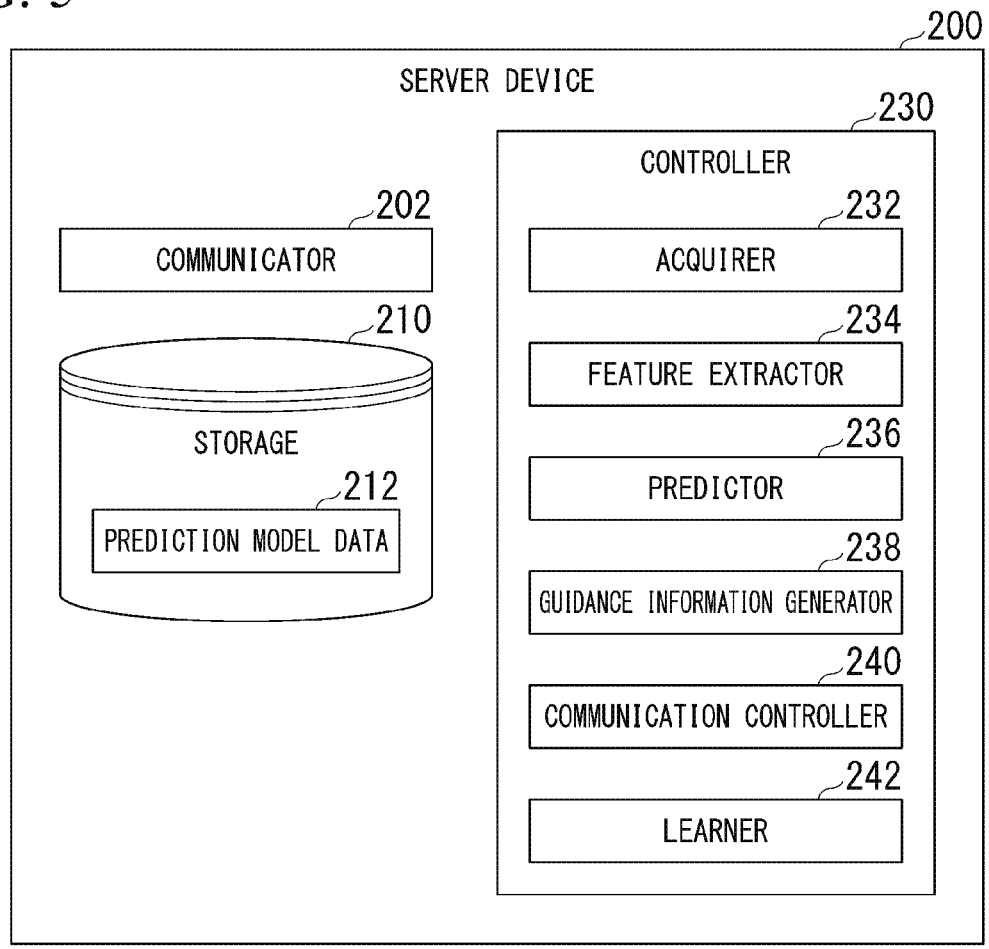
FIG. 5 is a diagram showing an example of a configuration of a server device according to the first embodiment.
FIG. 6 is a diagram showing an example of prediction model data.

FIG. 5 is a diagram showing an example of a configuration of the server device 200 according to the first embodiment. The server device 200 according to the first embodiment includes, for example, a communicator 202, a storage 210, and a controller 230. The configuration of the server device 200 shown in FIG. 5 is only an example, and a part of the configuration may be omitted or other components may be additionally added.

The communicator 202 includes a communication interface, for example, an antenna and an NIC. The communicator 202 communicates with the guide device 100 and the like via the network NW.

The storage 210 is realized by, for example, an HDD, a flash memory, an EEPROM, a ROM, or a RAM. In addition to a program that is referred to by a processor, for example, prediction model data 212 is stored in the storage 210.

The prediction model data 212 is information (a program or a data structure) in which one or a plurality of prediction models MDLs for predicting a predetermined event occurring in a moving body such as the vehicle M are defined. The prediction model MDL is, for example, a model that is learned to output a probability of a predetermined event that has occurred in the vehicle M that a user A drives (hereinafter referred to as an occurrence probability) when features related to driving characteristics of the user A are input.

The prediction model MDL may be realized using, for example, a deep neural network. In addition, the prediction model MDL is not limited to a deep neural network, and may be realized by other models such as logistic regression, support vector machine (SVM), k-nearest neighbor (k-NN) algorithm, decision tree, naïve Bayes classifier, and random forest.

FIG. 6 is a diagram showing an example of the prediction model data 212. As shown in the example in FIG. 6, the prediction model data 212 may be data in which a prediction model MDL is associated with a spot SP at which a predetermined event has occurred at least once in the past or a spot SP at which a predetermined event has occurred frequently in the past. The prediction model MDL associated with each spot SP is learned by a learner 242 to be described below. Here, the spot SP associated with the prediction model MDL may be treated as, on the map, a "point" as in a set of coordinates, treated as a "line" as in a road, or treated as a "plane" as in a municipality.

For example, the controller 230 includes an acquirer 232, a feature extractor 234, a predictor 236, a guidance information generator 238, a communication controller 240, and the learner 242. These components are realized, for example, when a processor such as a CPU and a GPU executes a program (software). In addition, some or all of these components may be realized by hardware (circuit unit; including a circuitry) such as an LSI, an ASIC, and an FPGA and may be realized in cooperation of software and hardware. The program may be stored in the storage 210 in advance or stored in a removable storage medium such as a DVD and a CD-ROM, and may be installed in the storage 210 when the storage medium is mounted in a drive device.

The acquirer 232 acquires driving data and profile data from the guide device 100 via the communicator 202.

The feature extractor 234 extracts features related to driving characteristics of the occupant from each of the driving data and profile data acquired by the acquirer 232.

The predictor 236 predicts that a predetermined event will occur in the vehicle M (hereinafter referred to as a "prediction target vehicle M") from which driving data and profile data are acquired based on the features extracted by the feature extractor 234. For example, the predictor 236 may input the features extracted by the feature extractor 234 to a prediction model MDL defined by the prediction model data 212, and predict whether a predetermined event will occur based on the occurrence probability output from the prediction model MDL. The prediction target vehicle M is an example of "first moving body."

Figure 7:
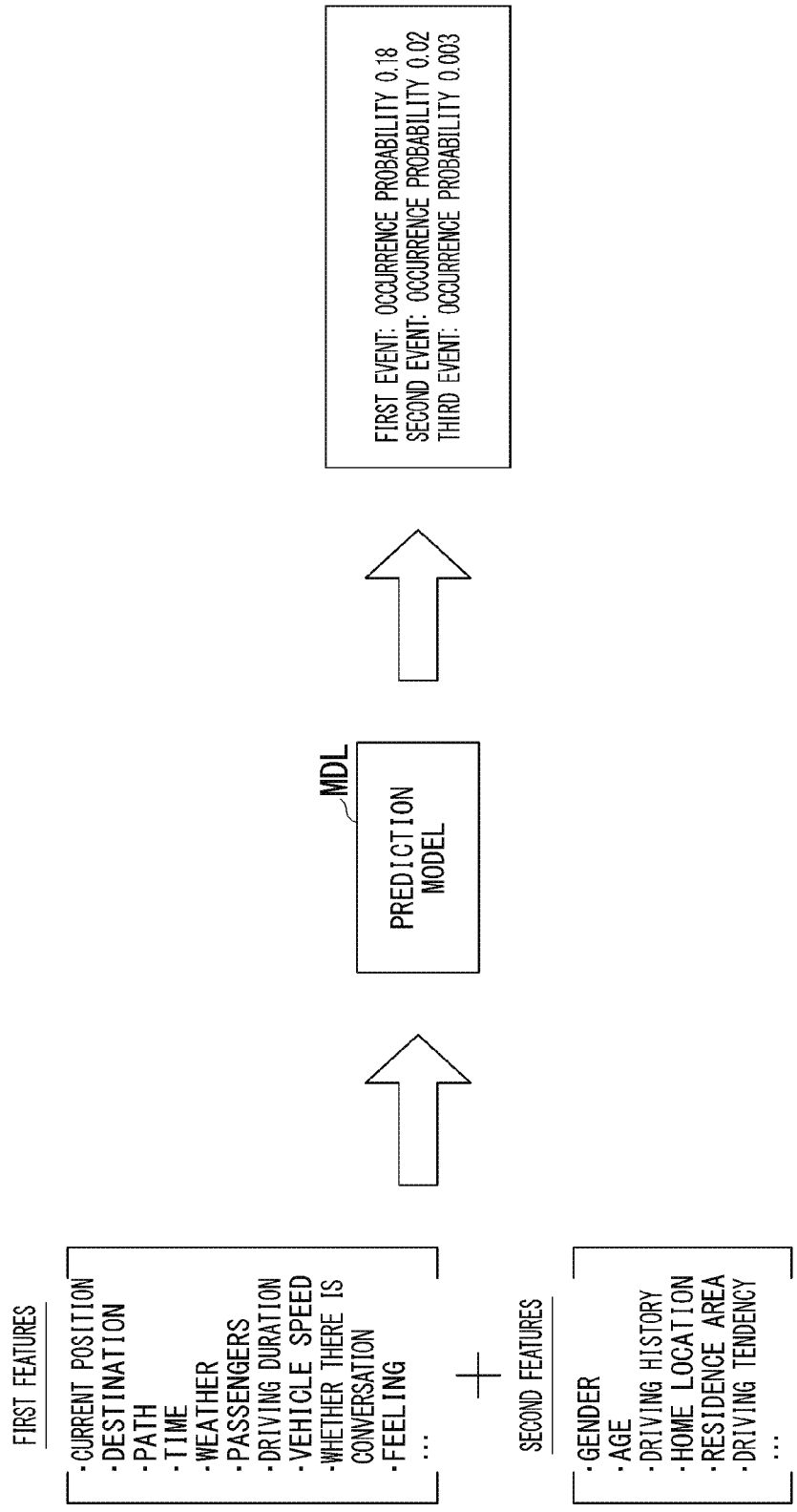
FIG. 7 is a diagram showing prediction of occurrence of a predetermined event.

FIG. 7 is a diagram showing prediction of occurrence of a predetermined event. As shown in the example in FIG. 7, the features extracted by the feature extractor 234 include first features extracted from the driving data and second features extracted from the profile data.

For example, the first features may include a current position, a destination, a traveling route, a time, the weather, the number of passengers, a duration for which an occupant has driven, a vehicle speed at a certain time, a vehicle speed history for a certain period, whether there is conversation in the vehicle, the feelings of the occupant at a certain time, an occupant feeling history during a certain period, a vehicle type, and the like. The second features include the gender, age, driving history, home location, residence area, driving tendencies, and the like.

Since such features are input to the prediction model MDL, the prediction model MDL derives the occurrence probability of a predetermined event, for example, based on situations in which, when it is raining, the speed of the prediction target vehicle M is high, the vehicle M is traveling on a route different from a route of traveling in a general residential area, the driver who drives the prediction target vehicle M is old, there is a tendency to start suddenly due to irritability, and additionally, there is a tendency to forget to check side mirrors because the driver is talking to other occupants in the vehicle.

For example, when the first features and second features described above are input, the prediction model MDL may output an occurrence probability of each of a plurality of events that is predicted in advance as predetermined events. Specifically, it is assumed that the predetermined event predicted in advance includes a first event in which a vehicle comes in contact with a pedestrian during turning right or left, a second event in which a vehicle enters an intersection against a red light, and a third event in which a vehicle comes in contact with a preceding vehicle. In this case, the prediction model MDL may set the first event, the second event, and the third event as elements and output a vector V (for example, V=[P1, P2, P3]) in which an element value corresponding to the element of the first event is set as an occurrence probability P1 of the first event, an element value corresponding to the element of the second event is set as an occurrence probability P2 of the second event, and an element value corresponding to the element of the third event is set as an occurrence probability P3 of the third event.

When the prediction model MDL outputs a vector representing occurrence probabilities of events, the predictor 236 predicts whether a predetermined event will occur based on the element values of the elements included in the vector, that is, the occurrence probabilities of the events. For example, when the largest occurrence probability is P1 and the occurrence probability P1 is equal to or larger than a certain threshold value $TH_P$, the predictor 236 may predict that the first event associated with the occurrence probability P1 will occur. In addition, when there are a plurality of occurrence probabilities that are equal to or larger than the threshold value $TH_P$, the predictor 236 may predict substantially at the same time that a plurality of events will occur. In addition, when all of the occurrence probabilities included in the vector are less than the threshold value $TH_P$, the predictor 236 may predict that the predetermined events will not occur.

When the predictor 236 predicts that a predetermined event will occur, the guidance information generator 238 generates guidance information according to the type of the event predicted to occur. For example, when the occurrence probability P1 of the first event is equal to or larger than the threshold value $TH_P$ and the first event is predicted to occur in the prediction target vehicle M, the guidance information generator 238 generates guidance information for prompting the occupant in the prediction target vehicle M to pay attention about the occurrence of the first event or prompting to change the route to another route (an example of a second route) in which the first event is less likely to occur.

When guidance information is generated by the guidance information generator 238, the communication controller 240 transmits the guidance information to the guide device 100 mounted in the prediction target vehicle M via the communicator 202.

The learner 242 learns the prediction model MDL. A method of learning the prediction model MDL will be described below.

[Processing Flow of Server Device]

Figure 8:
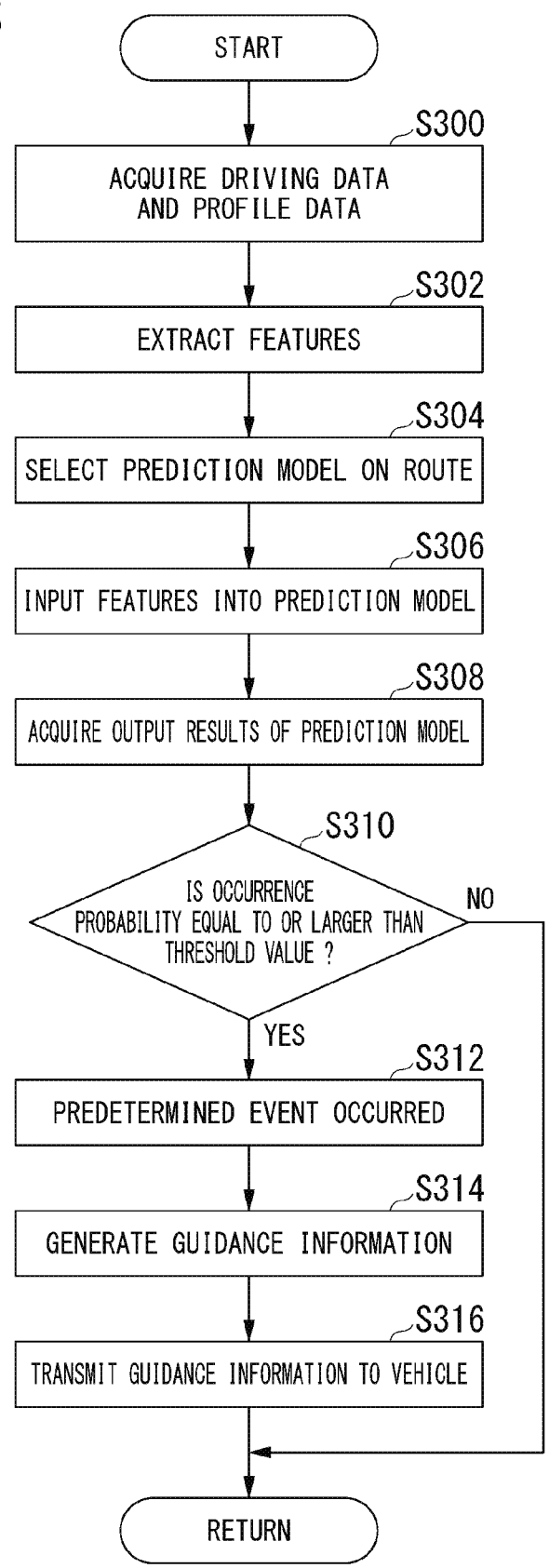
FIG. 8 is a flowchart showing a flow of a series of processes of the server device according to the first embodiment.

Processes of the server device 200 according to the first embodiment will be described below with reference to a flowchart. FIG. 8 is a flowchart showing a flow of a series of processes of the server device 200 according to the first embodiment. The process of this flowchart may be repeated at predetermined time intervals.

First, the acquirer 232 acquires driving data and profile data from the guide device 100 via the communicator 202 (Step S300).

Next, the feature extractor 234 extracts first features from the driving data and extracts second features from the profile data, which are acquired by the acquirer 232 (Step S302).

Next, the predictor 236 reads (acquires) the prediction model data 212 from the storage 210, and selects a prediction model MDL associated with a spot on a traveling route (that is, on a route scheduled to be traveled on before the prediction target vehicle M reaches the destination) included in the driving data or near the route (for example, within several tens of meters) from one or more prediction models MDLs included in the read prediction model data 212 (Step S304).

Figure 9:
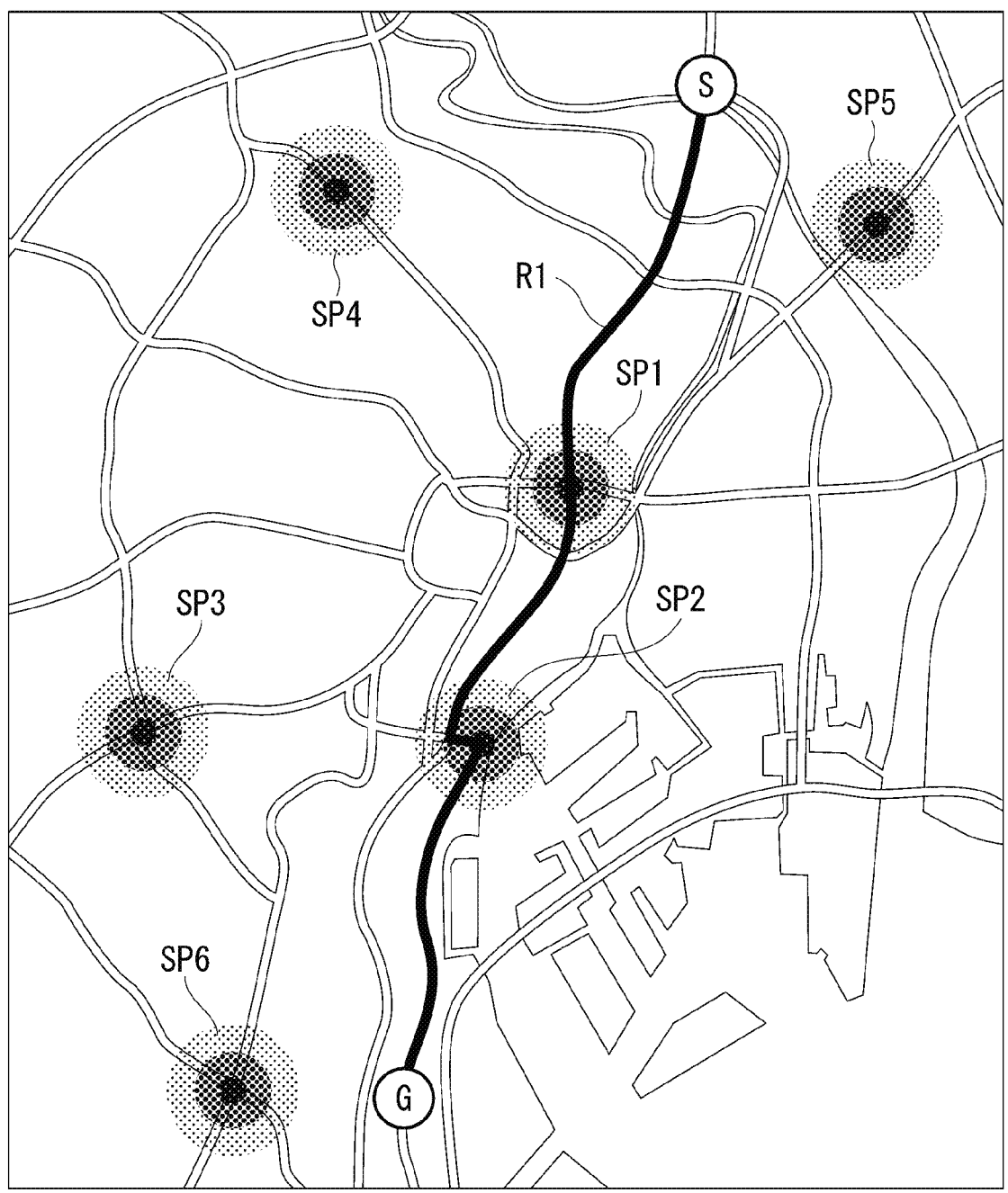
FIG. 9 is a diagram showing a prediction model selecting process.

FIG. 9 is a diagram showing a prediction model MDL selecting process. As shown in FIG. 9, for example, when a predetermined event has occurred in the past at each of a first spot SP1, a second spot SP2, a third spot SP3, a fourth spot SP4, a fifth spot SP5, and a sixth spot SP6, a prediction model MDL is associated with each of the spots SPs. In this case, the predictor 236 selects a prediction model MDL associated with a spot on a traveling scheduled route R1 for the prediction target vehicle M or near the route R1 from among 6 prediction models MDLs. In the shown example, the first spot SP1 and the second spot SP2 are present on the route R1 from a current position S to a destination G. Therefore, the predictor 236 selects a prediction model MDL1 associated with the first spot SP1 and a prediction model MDL2 associated with the second spot SP2 from among 6 prediction models MDLs.

The description will return to the flowchart in FIG. 8. Next, when a prediction model MDL is selected, the predictor 236 inputs features extracted by the feature extractor 234 to each selected prediction model MDL (Step S306).

Next, the predictor 236 acquires an output result of each prediction model MDL to which features are input, that is, a derivation result of the occurrence probability of the predetermined event at each spot (Step S308).

Next, the predictor 236 determines whether the occurrence probability of the predetermined event at each spot is equal to or larger than the threshold value $TH_P$ (Step S310). For example, when the occurrence probability output from the prediction model MDL1 associated with the first spot SP1 and the occurrence probability output from the prediction model MDL2 associated with the second spot SP2 both are less than the threshold value $TH_P$, the predictor 236 predicts that the predetermined event will not occur in the prediction target vehicle M even if traveling on the traveling scheduled route R1 and ends the process of this flowchart.

On the other hand, when the occurrence probability of the predetermined event at any one or a plurality of spots is equal to or larger than the threshold value $TH_P$, the predictor 236 predicts that the predetermined event will occur in the prediction target vehicle M before it reaches the destination (Step S312). The spot at which the occurrence probability of the predetermined event is equal to or larger than the threshold value $TH_P$ is an example of "occurrence position of the predetermined event," and the predictor 236 is an example of "first acquirer."

For example, when any one or both of the occurrence probability output from the prediction model MDL1 associated with the first spot SP1 and the occurrence probability output from the prediction model MDL2 associated with the second spot SP2 are equal to or larger than the threshold value $TH_P$, the predictor 236 predicts that a predetermined event will occur in the prediction target vehicle M when traveling on the traveling scheduled route R1.

Next, the guidance information generator 238 generates guidance information according to the type of the event that is predicted to occur by the predictor 236 (Step S314).

Figure 10:
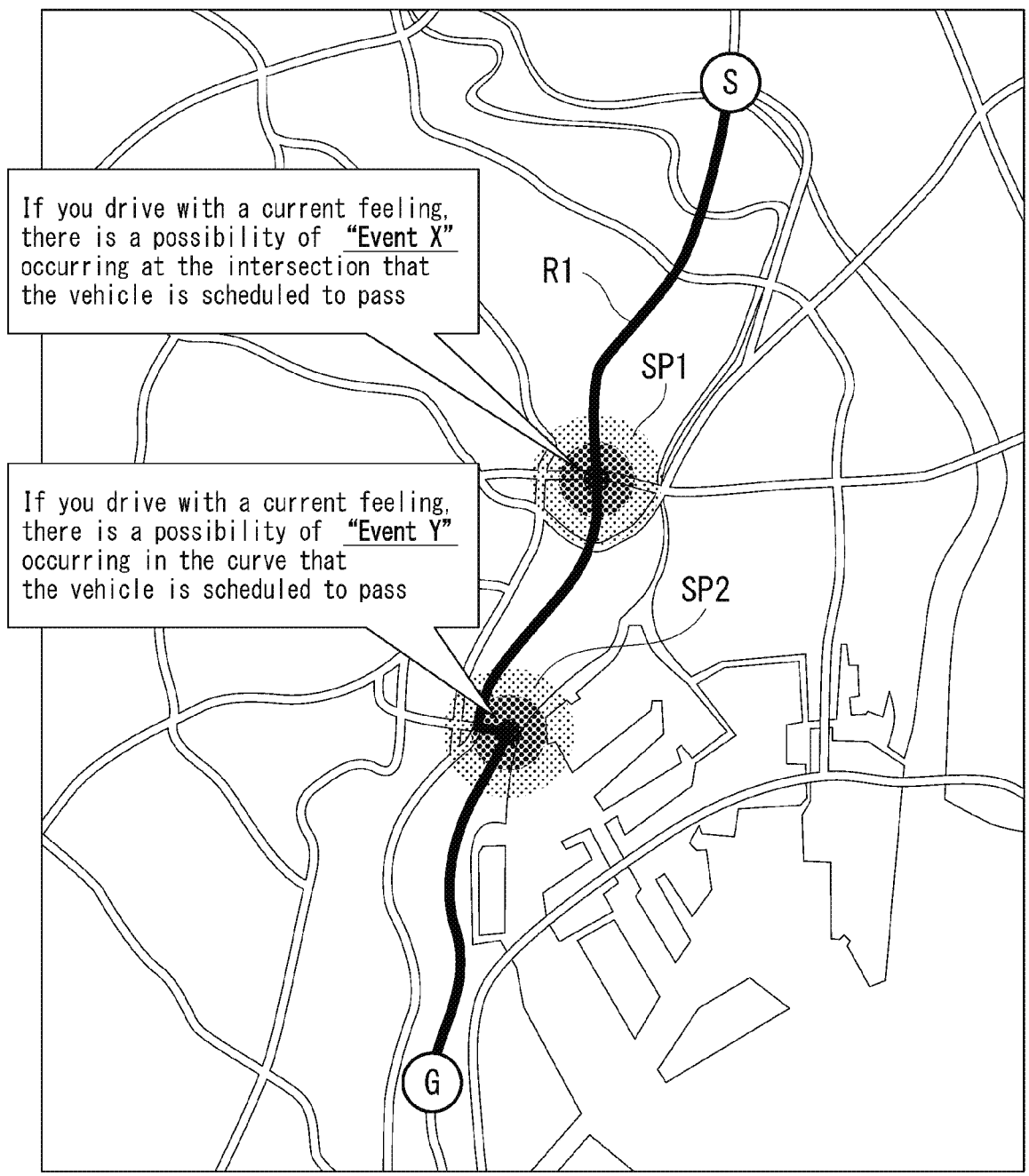
FIG. 10 is a diagram schematically showing an example of guidance information.

FIG. 10 is a diagram schematically showing an example of guidance information. For example, it is assumed that, when the first spot SP1 and the second spot SP2 at which the predetermined event has occurred in the past are present on the scheduled route R1 along which the prediction target vehicle is traveling, and the prediction target vehicle M travels on the route R1, the predictor 236 predicts that the predetermined event will occur at each of the first spot SP1 and the second spot SP2.

In this case, the guidance information generator 238 changes guidance information to be generated according to the type of the event predicted to occur at the first spot SP1 and the type of the event predicted to occur at the second spot SP2.

For example, as shown in FIG. 10, when an "event X" is predicted to occur at the first spot SP1, if the driver reaches the first spot SP1 while maintaining the current feeling or if the driver reaches the first spot SP1 with a certain specific feeling transition including a first feeling at the intersection three points before the first spot SP1, a second feeling at the intersection two points before the first spot SP1, and a third feeling at the intersection one point before the first spot SP1, the guidance information generator 238 may generate a map on which text and an image representing that there is a possibility of the "event X" occurring is superimposed on the first spot SP1 as guidance information.

Similarly, for example, as shown in FIG. 10, when an "event Y" is predicted to occur at the second spot SP2, if the driver reaches the second spot SP2 while maintaining the current feeling or if the driver reaches the second spot SP2 with a certain specific feeling transition, the guidance information generator 238 may generate a map on which text and an image representing that there is a possibility of the "event Y" occurring is superimposed on the second spot SP2 as guidance information.

In this manner, the guidance information generator 238 displays a spot at which the predetermined event is likely to occur when the driver continues driving with the current feeling on the map, and thus can prompt the occupant in the prediction target vehicle M to change the "feeling" that is one of generation factors (features) of the predetermined event. As a result, it is possible to reduce the occurrence of the predetermined event.

In addition, in place of or in addition to the "feeling" which is one of generation factors of the predetermined event, the guidance information generator 238 may generate guidance information for prompting to change the "vehicle speed" which is another factor, prompting to stop "conversation" with other passengers, prompting to take a break in order to shorten "driving duration," and prompting to change "path" and "destination."

Figure 11:
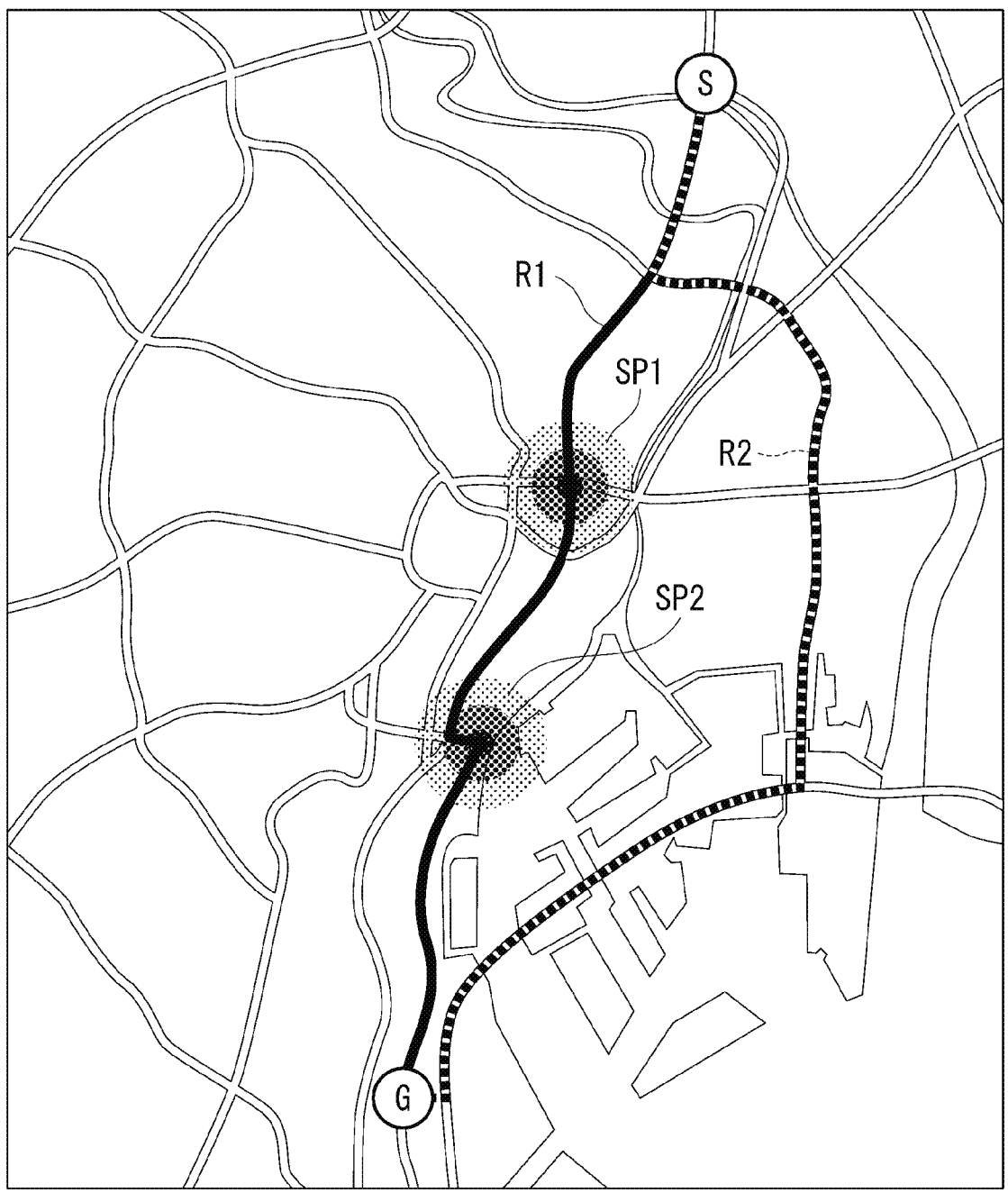
FIG. 11 is a diagram schematically showing another example of guidance information.

FIG. 11 is a diagram schematically showing another example of guidance information. As shown in the example in FIG. 11, when the first spot SP1 and the second spot SP2 at which the predetermined event is predicted to occur are present on the route R1 along which the prediction target vehicle M is scheduled to travel, the guidance information generator 238 generates guidance information for prompting to change the route to another route. For example, the guidance information generator 238 selects a route having few spots SPs at which the predetermined event is predicted to occur or having a smaller average or sum of occurrence probabilities of the predetermined event in the entire route than the current route from among a plurality of other routes from the current position S to the destination G. In this case, the predictor 236 predicts whether the predetermined event will occur for each route which is a candidate for a change destination. For example, when a route R2 is selected as a route having few occurrence spots of the predetermined event or a low occurrence probability of the predetermined event from among a plurality of other routes from the current position S to the destination G, the guidance information generator 238 may generate guidance information for prompting to change the route from the route R1 along which travel is scheduled to the selected route R2.

In addition, the guidance information generator 238 may change guidance information to be generated according to each of the occurrence probability of the event predicted to occur at the first spot SP1 and the occurrence probability of the event predicted to occur at the second spot SP2.

Figure 12:
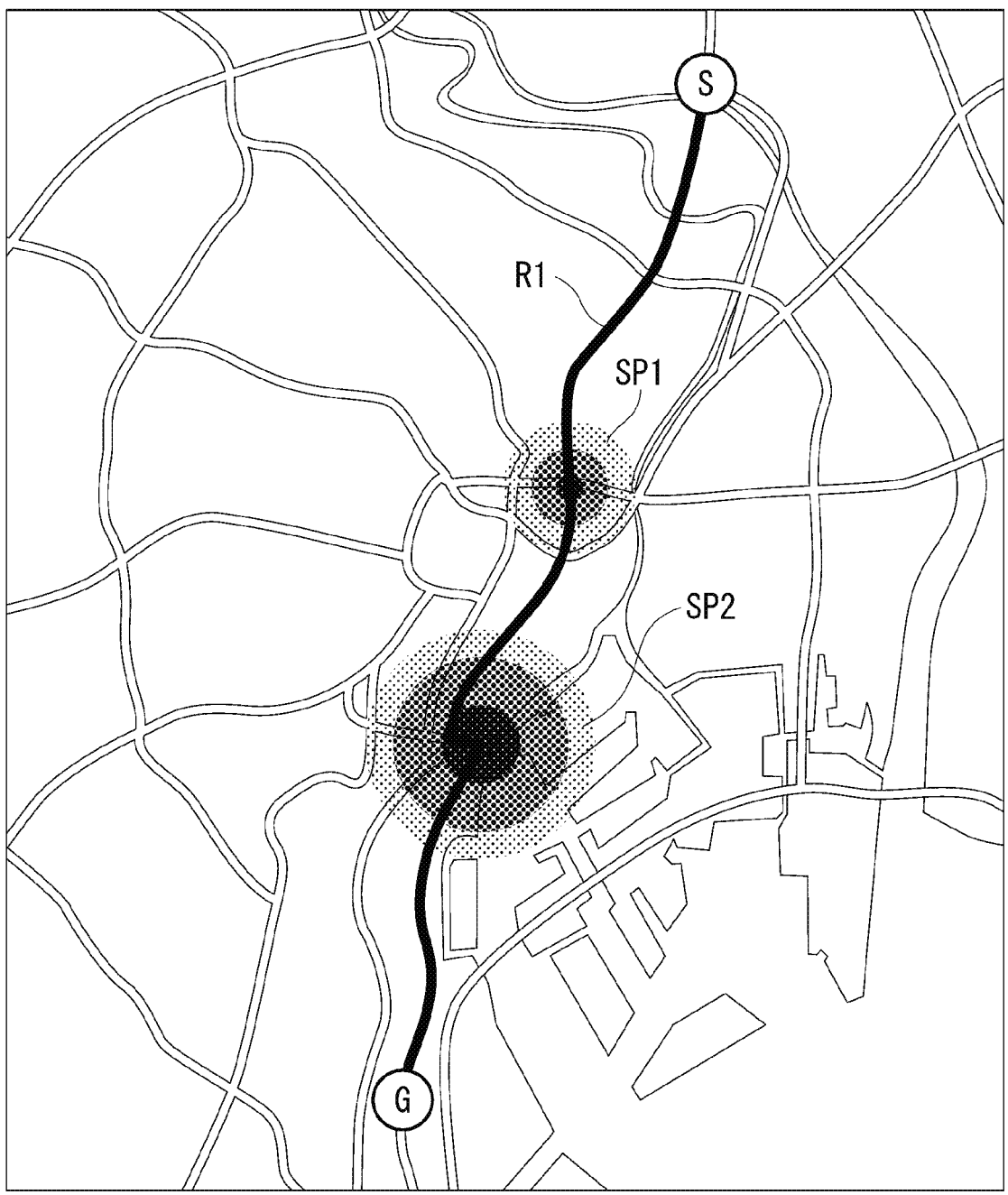
FIG. 12 is a diagram schematically showing another example of guidance information.

FIG. 12 is a diagram schematically showing another example of guidance information. For example, similarly to the other examples described above, it is assumed that the "event X" is predicted to occur at the first spot SP1 and the "event Y" is predicted to occur at the second spot SP2. In this case, for example, the guidance information generator 238 may generate a heat map on which occurrence points of events are colored in a color that easily attracts people's attention such as red or yellow when the occurrence probability of each event is higher as guidance information. For example, when the occurrence probability of the "event Y" predicted to occur at the second spot SP2 is higher than the occurrence probability of the "event X" predicted to occur at the first spot SP1, as shown in the example in FIG. 12, the guidance information generator 238 may make the color of the second spot SP2 darker than that of the first spot SP1 or make a region colored in red or yellow larger in the heat map.

The description will return to the flowchart in FIG. 8. Next, the communication controller 240 transmits the guidance information generated by the guidance information generator 238 to the guide device 100 mounted in the prediction target vehicle M via the communicator 202 (Step S316). Thereby, the process of this flowchart ends.

When the communicator 112 receives the guidance information from the server device 200, the output controller 140 of the guide device 100 outputs the guidance information to the HMI 110. Specifically, the output controller 140 causes the display of the HMI 110 to display a heat map as exemplified in FIG. 10, FIG. 11, or FIG. 12, and calls the attention of the occupant in the host vehicle M, prompts a change of feeling, and prompts a change of the route. In addition, the route determiner 134 of the guide device 100 may change the route to a route having few occurrence spots of the predetermined event or a low occurrence probability of the predetermined event according to the guidance information.

In addition, the output controller 140 may cause the HMI 110 to output guidance information at a time at which the host vehicle M has reached a spot at which the predetermined event has occurred or may cause the HMI 110 to output guidance information at a time at which the host vehicle M has reached a spot a predetermined distance before the spot at which the predetermined event has occurred.

[Learning Process Flow]

Figure 13:
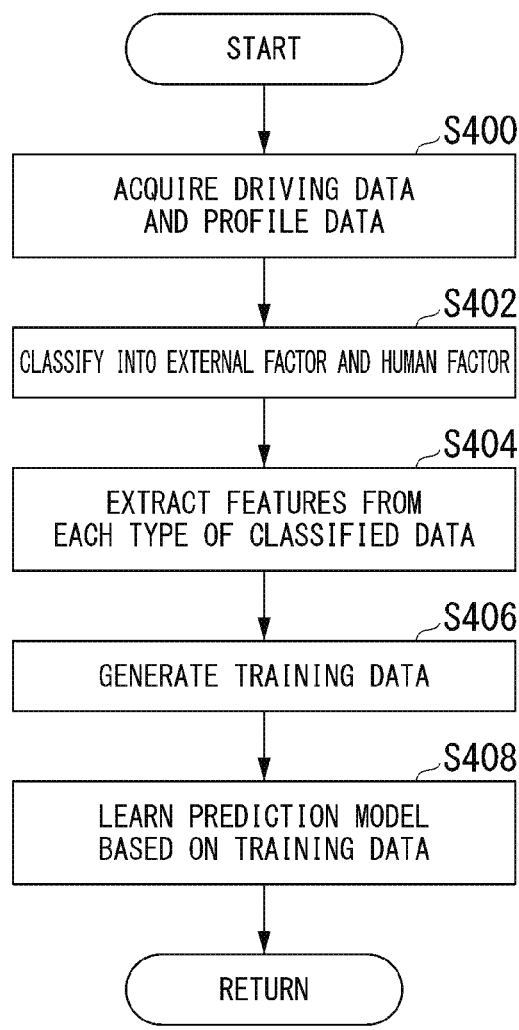
FIG. 13 is a flowchart showing a flow of a series of learning processes of the server device according to the first embodiment.
Figure 14:
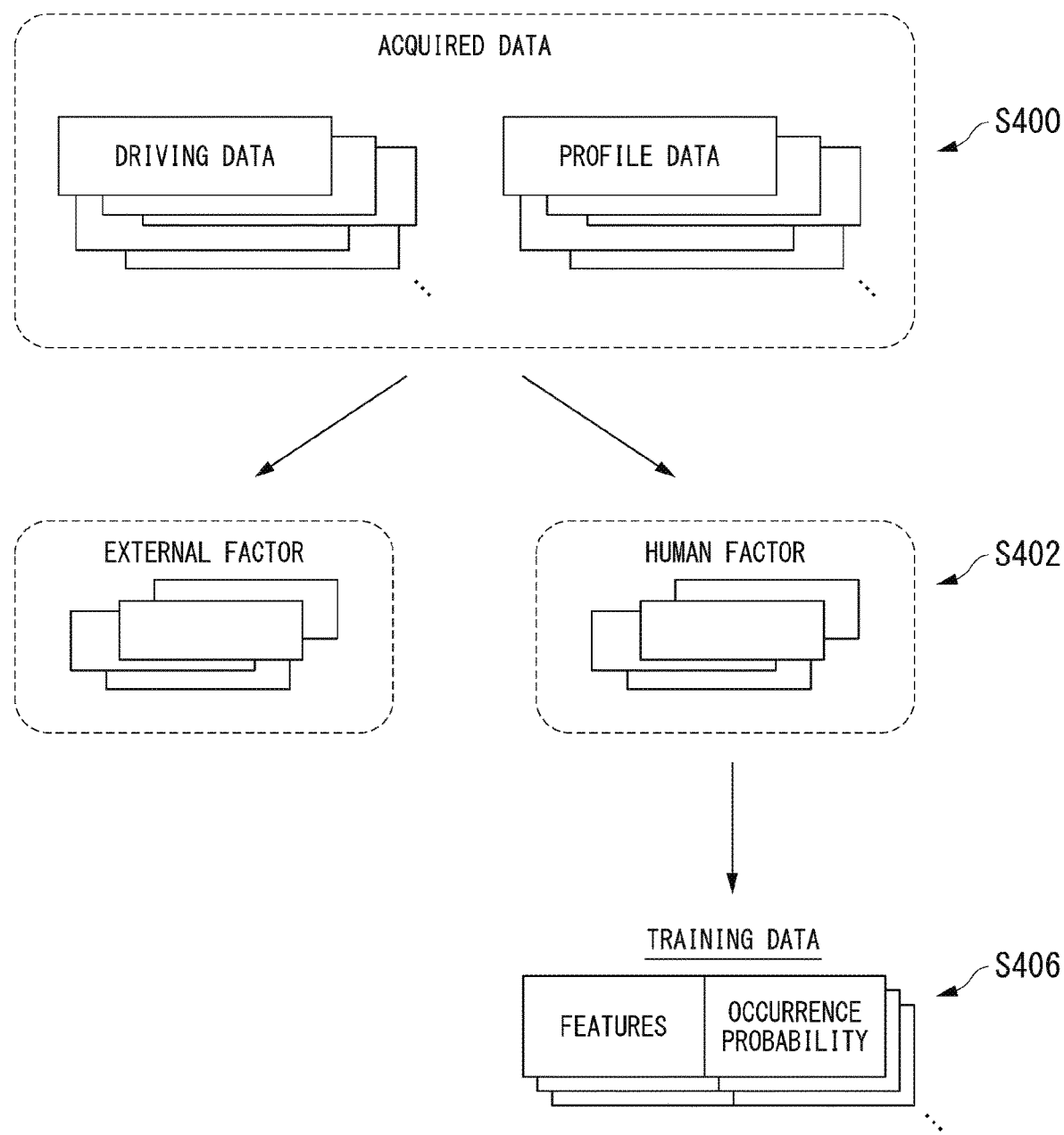
FIG. 14 is a diagram schematically showing an example of a learning process of the server device according to the first embodiment.

A learning process of the server device 200 according to the first embodiment will be described below with reference to a flowchart and a schematic diagram. FIG. 13 is a flowchart showing a flow of a series of learning processes of the server device 200 according to the first embodiment. In addition, FIG. 14 is a diagram schematically showing an example of a learning process of the server device 200 according to the first embodiment. The process of this flowchart may be repeated at predetermined time intervals.

First, the acquirer 232 acquires driving data and profile data from the guide devices 100 of an unspecified large number of vehicles M in which the predetermined event has occurred via the communicator 202 (Step S400).

Next, the learner 242 classifies a plurality of pieces of driving data and profile data acquired by the acquirer 232 in the process of S400 into a data group in which the predetermined event has occurred due to an external cause and a data group in which the predetermined event has occurred due to a human cause (Step S402).

For example, the learner 242 classifies driving data and profile data of the vehicle M that has caused the predetermined event in situations in which the road has good visibility like a straight road, the weather is good such as clear skies, and the driving duration is very long as a data group based on human factors, and classifies driving data and profile data of the vehicle M that has caused the predetermined event in situations in which the road has poor visibility like a curved road, the weather is bad such as rain, snow, or fog, and the driving duration is short as a data group based on external factors. Here, the learner 242 does not need to classify data that cannot be clearly classified according to whether it is based on external factors or human factors into any data group.

Next, the feature extractor 234 extracts features from driving data and profile data classified into a data group based on human factors such as a person's feeling among two classified data groups (Step S404). The features include first features extracted from driving data and second features extracted from profile data as described above.

Next, the learner 242 generates training data for learning a prediction model MDL associated with a spot at which the predetermined event has occurred using the features extracted by the feature extractor 234 in the process of S404 (Step S406).

For example, the learner 242 may generate training data in which an occurrence probability is associated as a training label for features extracted from the data group based on human factors by the feature extractor 234. For example, the learner 242 may set the occurrence probability to 1 based on the fact that the predetermined event has occurred.

Next, the learner 242 learns the prediction model MDL based on the generated training data and generates the prediction model data 212 in which the learned prediction model MDL is associated with the occurrence spot SP of the predetermined event (Step S408).

For example, the learner 242 inputs features included in the training data to the prediction model MDL and derives a difference between the occurrence probability output from the prediction model and the occurrence probability associated as a training label for features input to the prediction model MDL. Then, the learner 242 determines parameters such as a weighting factor and a bias component of the prediction model MDL using a probabilistic gradient method or the like so that the derived difference becomes smaller.

The prediction model MDL for which parameters are determined according to learning in this manner outputs a value closer to 1 as the occurrence probability of the predetermined event when features similar to the features input during learning are input. For example, when the event X which is one of the predetermined events occurs in a certain vehicle A, the occupant in the vehicle A feels irritated or frustrated. If the prediction model MDL is learned using the driving data and profile data obtained in such a situation, when another vehicle B with an occupant who feels irritated or frustrated similarly drives through a spot at which the event X has occurred, the learned prediction model MDL also outputs an occurrence probability indicating that there is a high probability of the occurrence of the same event X that has occurred in the vehicle A to the other vehicle B.

In addition, features of training data used for learning the prediction model MDL include a traveling route along which the vehicle M has traveled before it reaches a spot at which the predetermined event has occurred and a history of the feelings of the occupant in the vehicle M before it reaches a spot at which the predetermined event has occurred. Therefore, for example, when the following conditions (I) and (II) are satisfied, the prediction model MDL is likely to output a probability equal to or larger than the threshold value $TH_P$ as the occurrence probability of the predetermined event. Thereby, guidance information is likely to be output to the HMI 110 of the guide device 100.

Condition (I): When a prediction target vehicle M approaches a spot at which the predetermined event has occurred in the past, the prediction target vehicle M travels on the same route as the traveling route for the vehicle M that has caused the predetermined event. That is, the prediction target vehicle M is positioned on the traveling route for the vehicle M in which the predetermined event has occurred.

Condition (II): When a prediction target vehicle M approaches a spot at which the predetermined event has occurred in the past, the transition of the feelings of the occupant in the prediction target vehicle M has the same tendency as the transition of the feelings of the occupant in the vehicle M that has caused the predetermined event. That is, the history of the feelings of the occupant in the vehicle M that has caused the predetermined event includes feelings of the occupant in the prediction target vehicle M.

In addition, features of training data used for learning the prediction model MDL further include a history of the speed of the vehicle M before it reaches a spot at which the predetermined event has occurred. Therefore, for example, if the condition (III) is additionally satisfied in addition to one or both of the above conditions (I) and (II), the prediction model MDL is more likely to output a probability equal to or larger than the threshold value $TH_P$ as the occurrence probability of the predetermined event. Thereby, guidance information is likely to be output to the HMI 110 of the guide device 100.

Condition (III): When a prediction target vehicle M approaches a spot at which the predetermined event has occurred in the past, the transition of the speed of the prediction target vehicle M has the same tendency as the transition of the speed of the vehicle M that has caused the predetermined event. That is, the history of the speed of the vehicle M that has caused the predetermined event includes the speed of the prediction target vehicle M.

In addition, since features of training data used for learning the prediction model MDL further include weather, for example, when the condition (IV) is additionally satisfied in addition to one to all of the above conditions (I) to (III), the prediction model MDL is more likely to output a probability equal to or larger than the threshold value $TH_P$ as the occurrence probability of the predetermined event. Thereby, guidance information is likely to be output to the HMI 110 of the guide device 100.

Condition (IV): Weather when a prediction target vehicle M approaches a spot at which the predetermined event has occurred in the past is the same as the weather when the predetermined event has occurred.

In addition, since features of training data used for learning the prediction model MDL further include time, for example, when the condition (V) is additionally satisfied in addition to one or all of the above conditions (I) to (IV), the prediction model MDL is more likely to output a probability equal to or larger than the threshold value $TH_P$ as the occurrence probability of the predetermined event. Thereby, guidance information is likely to be output to the HMI 110 of the guide device 100.

Condition (V): The time at which a prediction target vehicle M approaches a spot at which the predetermined event has occurred in the past is the same as the time at which the predetermined event has occurred.

In addition, when generation factors of a plurality of predetermined events that have occurred at different spots SPs include the fact that the occupant who drives the vehicle M felt "irritated" or "frustrated,", that is, when the generation factors of a plurality of predetermined events include a predetermined tendency of the driver to feel "irritated" or "frustrated," the learner 242 may associate the same prediction model MDL with the occurrence spots SPs of the plurality of predetermined events.

Figure 15:
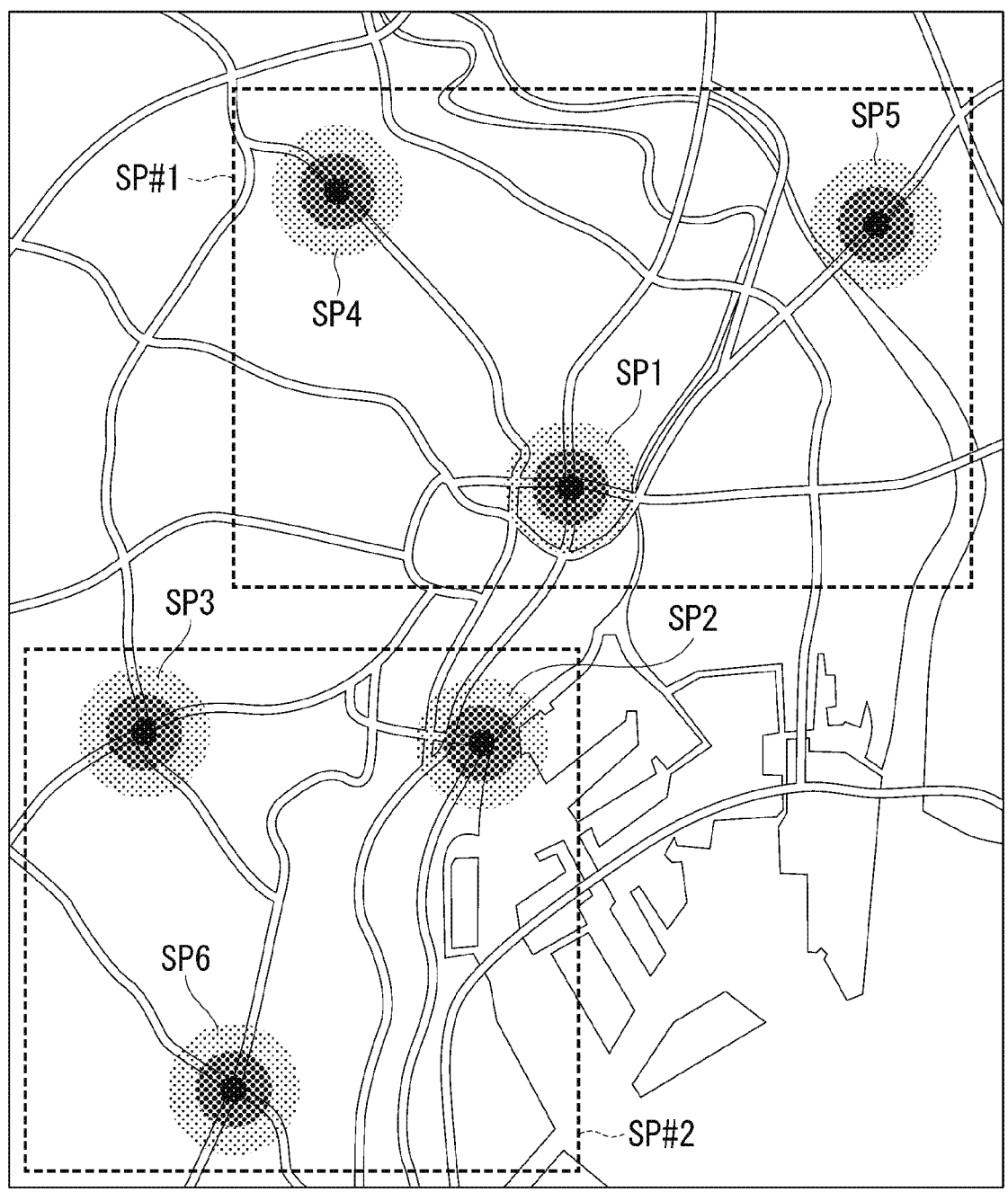
FIG. 15 is a diagram schematically showing a state in which a predetermined event occurs at a plurality of spots.

FIG. 15 is a diagram schematically showing a state in which the predetermined event occurs at a plurality of spots. The example in FIG. 15 shows that the predetermined event has occurred at a total of 6 spots including SP1 to SP6. For example, the driver's feeling which is a generation factor of the predetermined event has the same tendency at 3 spots including SP1, SP4, and SP5, and the driver's feeling which is a generation factor of the predetermined event has the same tendency at 3 spots including SP2, SP3, and SP6. In this case, the learner 242 generates the prediction model data 212 in which 3 spots including SP1, SP4, and SP5 are treated as one global area SP #1 and a prediction model MDL of any of SP1, SP4, and SP5 is associated with the area SP #1. In addition, the learner 242 generates the prediction model data 212 in which 3 spots including SP2, SP3, and SP6 are treated as one global area SP #2 and a prediction model MDL of any of SP2, SP3, and SP6 is associated with the area SP #2.

Thereby, when there is a prediction target vehicle M in the global area SP # (a region treated as a plane not a point) in which the feelings of occupants in the plurality of vehicles Ms in which the predetermined event has occurred have a predetermined tendency and the feelings of the occupant in the prediction target vehicle M have a predetermined tendency, the prediction model MDL associated with the global area SP # is more likely to output a probability equal to or larger than the threshold value $TH_P$ as the occurrence probability of the predetermined event. Thereby, guidance information is likely to be output to the HMI 110 of the guide device 100.

Here, the learner 242 may additionally generate training data using features extracted from a data group based on external factors and learn the prediction model MDL based on the generated training data. Thereby, it is possible to predict whether the predetermined event will occur due to a human factor such as a person's feeling and predict whether the predetermined event will occur due to an external factor such as the shape of the road and weather.

According to the first embodiment described above, guidance information for providing guidance regarding the fact that there is a possibility of the predetermined event occurring in a prediction target vehicle M based on the occurrence position of the predetermined event that occurred due to at least the feelings of the occupant in the vehicle and the position of the certain prediction target vehicle M to the occupant in the prediction target vehicle M is output by the HMI 110, and thus it is possible to inform the occupant in the vehicle M that an unexpected and unforeseen situation can occur and to prepare the occupant in the vehicle M for the unforeseen situation.

In addition, according to the first embodiment described above, since the HMI 110 is caused to output guidance information for prompting to change feeling, it is possible to reduce the occurrence of the unforeseen situation that can occur due to a person's feeling.

In addition, according to the first embodiment described above, since the HMI 110 is caused to output guidance information for prompting to change the route to a route on which the predetermined event is less likely to occur, it is possible to reduce the occurrence of the unforeseen situation that can occur due to a person's feeling.

Modified Example of First Embodiment

A modified example of the first embodiment will be described below. While the guide device 100 mounted in each vehicle M and the server device 200 that are devices different from each other have been described in the above first embodiment, the present invention is not limited thereto, and some or all of components of the guide device 100 may be included in the server device 200 and some or all of components of the server device 200 may be included in the guide device 100. For example, the server device 200 may be a component of the controller 130 of the guide device 100, that is, the server device 200 may be a virtual machine that is virtually realized by the controller 130 of the guide device 100.

Figure 16:
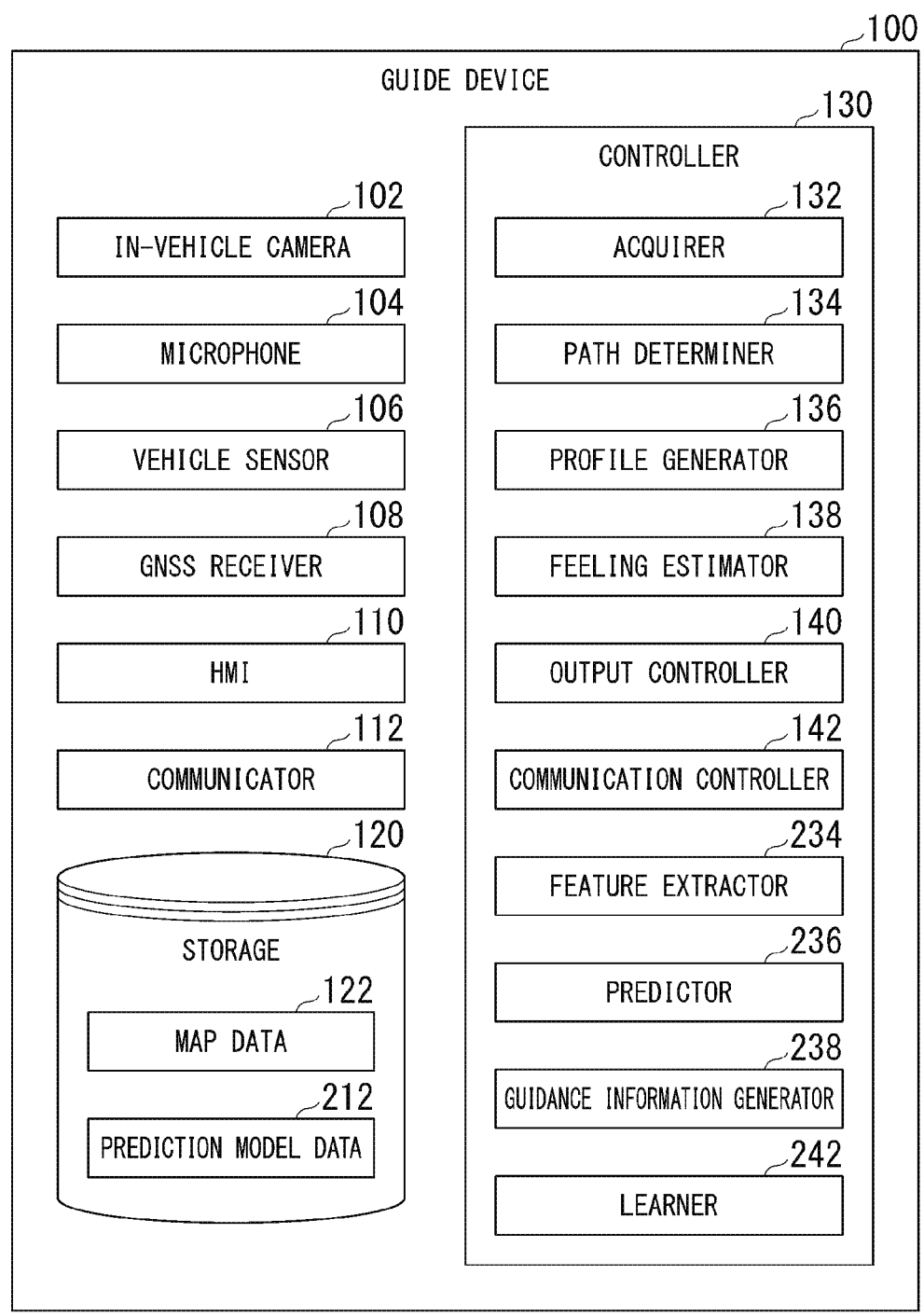
FIG. 16 is a diagram showing another example of the guide device according to the first embodiment.

FIG. 16 is a diagram showing another example of the guide device 100 according to the first embodiment. As shown in FIG. 16, the controller 130 of the guide device 100 may additionally include the feature extractor 234, the predictor 236, the guidance information generator 238, and the learner 242 in addition to the acquirer 132, the route determiner 134, the profile generator 136, the feeling estimator 138, the output controller 140, and the communication controller 142 described above.

In addition, in the storage 120 of the guide device 100, the prediction model data 212 may be additionally stored in addition to the map data 122.

In such a configuration, since it is possible to predict whether the predetermined event will occur by the guide device 100 alone, it is possible to inform the occupant in the vehicle M that an unexpected accident can occur.

In addition, while a case in which, when the occurrence probability of the predetermined event output from the prediction model MDL is equal to or larger than the threshold value $TH_P$, guidance information for prompting the occupant to pay attention and prompting to change the route is output has been described in the above first embodiment, the present invention is not limited thereto. For example, the server device 200 may transmit guidance information to the guide device 100 even if the occurrence probability of the predetermined event output from the prediction model MDL is less than the threshold value $TH_P$. Thereby, for example, when the host vehicle M travels on a route on which many occupants are likely to feel irritated or frustrated and a distance between vehicles tends to be reduced, it is possible to notify the occupant in the host vehicle M of the fact that there is a high probability of the predetermined event caused by occupants in the surrounding other vehicles even in a situation in which the occupant in the host vehicle M drives calmly and steadily.

Second Embodiment

A second embodiment will be described below. A case in which the occurrence of the predetermined event is predicted using the learned prediction model MDL such as a deep neural network, logistic regression, and SVM has been described in the above first embodiment. On the other hand, the second embodiment is different from the above first embodiment in that a similarity between features extracted from driving data and profile data of the vehicle M that has caused the predetermined event and features extracted from driving data and profile data of the vehicle M scheduled to pass through a spot at which a predetermined event has occurred in the past is calculated, and the occurrence of the predetermined event is predicted according to the calculated similarity. Hereinafter, a description will focus on differences from the first embodiment and those the same as in the first embodiment will not be described. Here, in the description of the second embodiment, the same components as in the first embodiment will be denoted with the same reference numerals for description.

The predictor 236 of the server device 200 according to the second embodiment calculates a similarity between features extracted from driving data and profile data of the vehicle M that has caused the predetermined event and features extracted from driving data and profile data of the vehicle M scheduled to pass through a spot at which the predetermined event has occurred in the past.

For example, the predictor 236 calculates a similarity based on the inner product of two vectors in a certain vector space in which two features are formed into vectors. Specifically, the predictor 236 obtains a cosine similarity between two feature vectors and the occurrence probability is higher as the cosine similarity is larger, and the occurrence probability is smaller as the cosine similarity is lower. In such similarity calculation, learning of models such as a deep neural network, logistic regression, and SVM can be omitted, and it is possible to predict whether the predetermined event will occur with a simpler configuration.

Third Embodiment

Hereinafter, a third embodiment will be described. A case in which, when the occurrence of the predetermined event is predicted, the attention of the occupant is called, change of the feeling is prompted, change of the route is prompted or the route to the destination in which the host vehicle M is scheduled to travel is changed to a route having few occurrence spots of the predetermined event or a low occurrence probability of the predetermined event has been described in the above first embodiment or second embodiment. On the other hand, the third embodiment is different from the above first embodiment and second embodiment in that, when the occurrence of the predetermined event is predicted, the vehicle M is automatically driven and moved to a route having few spots at which the predetermined event occurs or having a lower occurrence probability of the predetermined event. Hereinafter, description will focus on differences from the first embodiment or the second embodiment, and those the same as in the first embodiment or the second embodiment will not be described. Here, in the description of the third embodiment, the same components as in the first embodiment and the second embodiment will be denoted with the same reference numerals for description.

Figure 17:
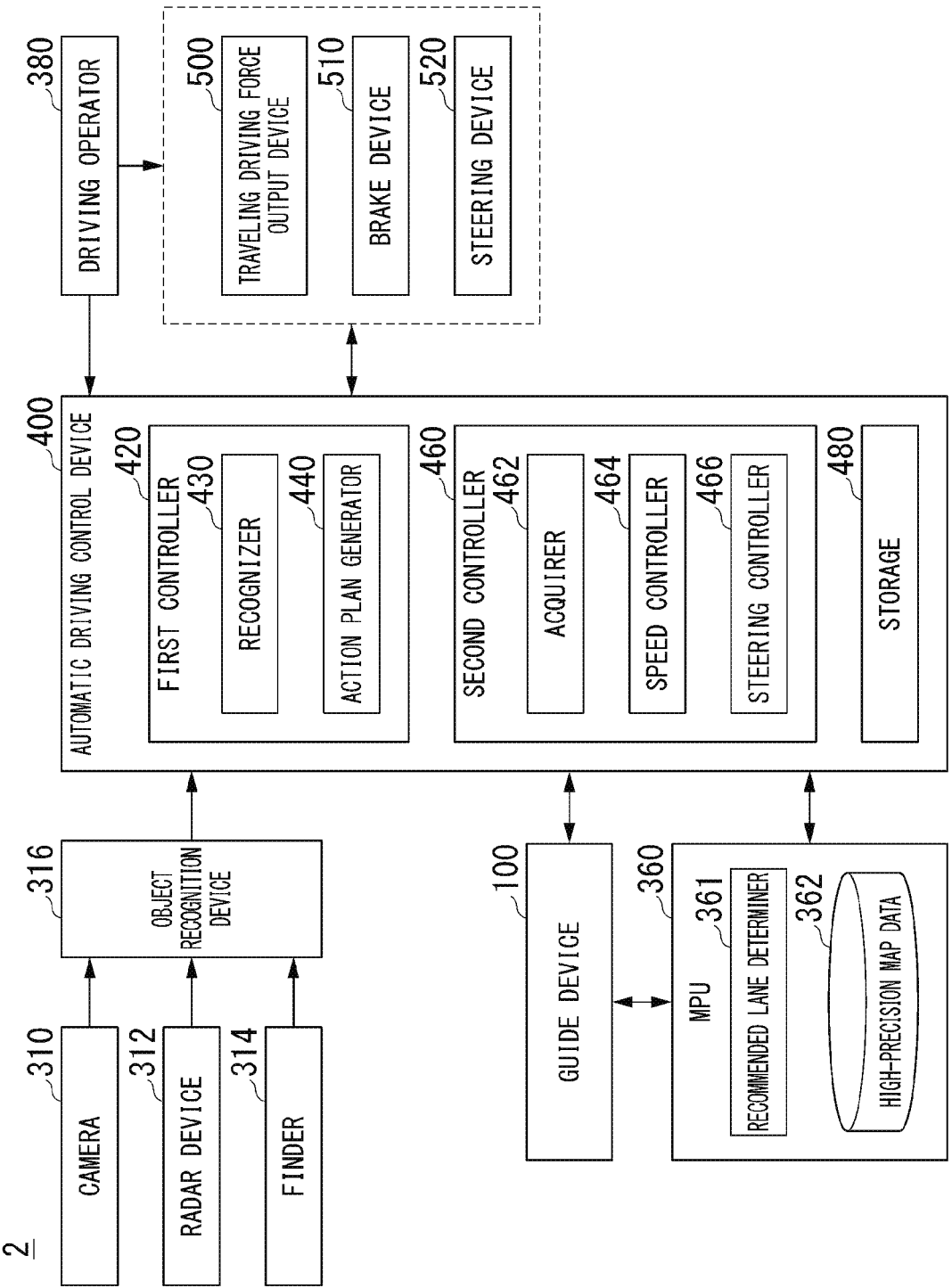
FIG. 17 is a configuration diagram of a vehicle system including a guide device according to a third embodiment.

FIG. 17 is a configuration diagram of a vehicle system 2 including the guide device 100 according to the third embodiment. The vehicle system 2 includes, for example, the guide device 100, a camera 310, a radar device 312, a finder 314, an object recognition device 316, a map positioning unit (MPU) 360, a driving operator 380, an automatic driving control device 400, a traveling driving force output device 500, a brake device 510, and a steering device 520. These devices and instruments are connected to one another via a multiplex communication line such as a controller area network (CAN) communication line, a serial communication line, a wireless communication network, or the like. Here, the configuration shown in FIG. 17 is only an example, and a part of the configuration may be omitted or other components may be additionally added.

For example, the camera 310 is a digital camera using a solid-state image sensing device such as a CCD and a CMOS. The camera 310 is attached to an arbitrary part of the host vehicle M in which the vehicle system 2 is mounted. When the camera 310 captures an image in front of the vehicle, it is attached to an upper part of the front windshield, a rear surface of the rearview mirror, or the like. For example, the camera 310 captures periodically and repeatedly the surroundings of the host vehicle M. The camera 310 may be a stereo camera.

The radar device 312 emits radio waves such as millimeter waves to the vicinity of the host vehicle M and detects radio waves (reflected waves) reflected at an object and detects at least a position (a distance and an orientation) of the object. The radar device 312 is attached to an arbitrary part of the host vehicle M. The radar device 312 may detect a position and speed of the object according to a frequency modulated continuous wave (FM-CW) method.

The finder 314 is a light detection and ranging (LIDAR) device. The finder 314 emits light to the vicinity of the host vehicle M and measures scattered light. The finder 314 detects a distance to the object based on a time from when light is emitted until light is received. Light to be emitted is, for example, a pulsed laser beam. The finder 314 is attached to an arbitrary part of the host vehicle M.

The object recognition device 316 performs sensor fusion processing on detection results obtained by some or all of the camera 310, the radar device 312, and the finder 314 and recognizes a position, type, speed, and the like of the object. The object recognition device 316 outputs the recognition result to the automatic driving control device 400. The object recognition device 316 may output the detection results of the camera 310, the radar device 312, and the finder 314 to the automatic driving control device 400 without change. The object recognition device 316 may be omitted from the vehicle system 2.

The MPU 360 includes, for example, a recommended lane determiner 361, and stores high-precision map data 362 in a storage device such as an HDD and a flash memory. The recommended lane determiner 361 divides the route to the destination determined by the guide device 100 into a plurality of blocks (for example, divide every 100 [m] with respect to the travelling direction of the vehicle), and determines a recommended lane in which the vehicle M should travel for each block with reference to the high-precision map data 362. The recommended lane determiner 361 determines in what number of a lane from the left to travel.

The high-precision map data 362 is map data with higher precision than the map data 122. The high-precision map data 362 includes, for example, information on the center of the lane, information on the boundary of the lane, and the like. In addition, the high-precision map data 362 may include road information, traffic regulation information, address information (address and zip code), facility information, phone number information, and the like. The high-precision map data 362 may be updated as necessary according to communication by a communication device 20 with other devices.

The driving operator 380 includes, for example, an accelerator pedal, a brake pedal, a shift lever, a steering wheel, a deformed steer, a joystick, and other operators. In the driving operator 380, a sensor configured to detect whether an operation is performed on the operator and detect a degree of operation performed on the operator as an operation amount is provided. When the sensor detects whether an operation is performed or an operation amount, it outputs data indicating the detection result to the automatic driving control device 400 or outputs the detection result to the traveling driving force output device 500, the brake device 510, and the steering device 520.

The automatic driving control device 400 includes, for example, a first controller 420, a second controller 460, and a storage 480. Each of the first controller 420 and the second controller 460 is realized by, for example, a processor such as a CPU and a GPU executes a program (software). In addition, some or all of these components may be realized by hardware (circuit unit; including a circuitry) such as an LSI, an ASIC, and an FPGA, or may be realized in cooperation of software and hardware. The program may be stored in an HDD, a flash memory, or the like of the storage 480 in advance, or may be stored in a removable storage medium such as a DVD and a CD-ROM, and may be installed in the storage 480 when the storage medium is mounted in a drive device. The automatic driving control device 400 is an example of "driving controller."

The storage 480 is realized by, for example, an HDD, a flash memory, an EEPROM, a ROM, or a RAM. In the storage 480, for example, a program that is read and executed by a processor is stored.

The first controller 420 includes, for example, a recognizer 430, and an action plan generator 440. For example, the first controller 420 realizes a function based on artificial intelligence (AI) and a function based on a model provided in advance in parallel. For example, a function of "recognizing an intersection" may be realized according to recognition of an intersection using deep learning and the like and recognition based on conditions provided in advance (pattern-matchable signals, road marks and the like) executed in parallel, and scoring and comprehensively evaluating them. Thereby, the reliability of the automatic driving is secured.

The recognizer 430 recognizes surrounding situations of the host vehicle M based on information input from the camera 310, the radar device 312, and the finder 314 through the object recognition device 316, that is, detection results obtained by sensor fusion. For example, the recognizer 430 recognizes the status such as the position, speed, and acceleration of the object present around the host vehicle M as surrounding situations. Examples of the object recognized for surrounding situations include moving bodies such as pedestrians and other vehicles and stationary components such as construction tools. The position of the object is recognized as a position on coordinates using, for example, the representative point (center of gravity, center of the drive shaft, or the like) of the host vehicle M as the origin and is used for control. The position of the object may be represented by a representative point such as the center of gravity or corner of the object or may be represented by a region having a spatial width. The "status" of the object may include the acceleration or jerk of the object or "action status" (for example, whether it is changing or about to change lanes).

In addition, for example, the recognizer 430 recognizes a lane in which the host vehicle M travels (hereinafter referred to as a host lane), an adjacent lane adjacent to the host lane, and the like as surrounding situations. For example, the recognizer 430 compares a pattern of road lane lines (for example, an arrangement of solid lines and broken lines) obtained from the high-precision map data 362 with a pattern of road lane lines around the host vehicle M recognized from the image captured by the camera 310 and thus recognizes the host lane and the adjacent lane. Here, the recognizer 430 may recognize the host lane and the adjacent lane by recognizing runway boundaries (road boundaries) including road lane lines, shoulders, curbstones, median strips, and guardrails without limitation to road lane lines. In this recognition, the position of the host vehicle M specified by the GNSS receiver 108 of the guide device 100 and the processing result by INS may be taken into consideration. In addition, the recognizer 430 may recognize sidewalks, stop lines (including temporary stop lines), obstacles, red lights, tollgates, road structure, and other road events.

When the host lane is recognized, the recognizer 430 recognizes the relative position and orientation of the host vehicle M with respect to the host lane. For example, the recognizer 430 may recognize the deviation of the reference point of the host vehicle M with respect to the center of the lane and an angle formed by a vector indicating the travelling direction of the host vehicle M and a line connecting the center of the lane as the relative position and orientation of the host vehicle M with respect to the host lane. Alternatively, the recognizer 430 may recognize the position of the reference point of the host vehicle M with respect to any side end (road lane line or road boundary) of the host lane as the relative position of the host vehicle M with respect to the host lane.

The action plan generator 440 determines an automatic driving event on a route on which a recommended lane is determined. In the automatic driving, without depending on the operation of the driving operator 380 performed by the occupant in the host vehicle M, one or both of the steering and speed of the host vehicle M are controlled so that the host vehicle M is driven. On the other hand, in manual driving, the steering and speed of the host vehicle M are controlled according to the operation of the occupant with respect to the driving operator 380. The automatic driving event is information that defines the behavior that the host vehicle M should take under the above automatic driving, that is, the driving mode.

Examples of events include a constant speed traveling event in which the host vehicle M is caused to travel in the same lane at a certain speed, a following traveling event in which the host vehicle M is caused to follow another vehicle (hereinafter referred to as a preceding vehicle) within a predetermined distance (for example, within 100 [m]) in front of the host vehicle M, and closest to the host vehicle M, a lane change event in which the lane of the host vehicle M is changed from the host lane to an adjacent lane, a branching event in which the lane of the host vehicle M is branched to the destination lane at a road branching location, a merging event in which the host vehicle M is merged to the main line at the merging location, an overtaking event in which the lane of the host vehicle M is changed to an adjacent lane once, and the lane is changed again to the original lane after passing the preceding vehicle in the adjacent lane, an avoidance event in which the host vehicle M is caused to perform at least one of braking and steering in order to avoid obstacles existing in front of the host vehicle M, and a takeover event in which automatic driving ends and is switched to manual driving. "Following" may be, for example, a driving mode in which a constant relative distance between the host vehicle M and the preceding vehicle (distance between vehicles) is maintained or a driving mode in which a relative distance between the host vehicle M and the preceding vehicle is maintained constant and also the host vehicle M is caused to travel to the center of the host lane.

The action plan generator 440 may change an event already determined for the current interval or the next interval to another event and determine a new event for the current interval or the next interval according to the surrounding situation recognized by the recognizer 430 when the host vehicle M travels.

In principle, the action plan generator 440 generates a future target trajectory in which the host vehicle M travels the recommended lane determined by the recommended lane determiner 361 and additionally, in order to respond the surrounding situations when the host vehicle M travels the recommended lane, the host vehicle M is caused to automatically (without depending on the operation of the driver) travel in the driving mode defined by the event. The target trajectory includes, for example, a position element that determines the future position of the host vehicle M and a speed element that determines the future speed, acceleration and the like of the host vehicle M.

For example, the action plan generator 440 determines a plurality of spots (trajectory point) at which the host vehicle M should reach sequentially as the position element of the target trajectory. The trajectory point is a spot at which the host vehicle M should reach for each predetermined traveling distance (for example, about several [m]). The predetermined traveling distance may be calculated by, for example, a distance along the route when the vehicle travels along the route.

In addition, the action plan generator 440 determines a target speed and a target acceleration for each predetermined sampling time (for example, 0 comma several seconds) as a speed element of the target trajectory. In addition, the trajectory point may be a position that the host vehicle M should reach at the sampling time for each predetermined sampling time. In this case, the target speed and target acceleration are determined by intervals of the sampling time and the trajectory point. The action plan generator 440 outputs information indicating the generated target trajectory to the second controller 460.

The second controller 460 controls some or all of the traveling driving force output device 500, the brake device 510, and the steering device 520 so that the host vehicle M passes through the target trajectory generated by the action plan generator 440 according to the scheduled time. That is, the second controller 460 causes the host vehicle M to be automatically driven based on the target trajectory generated by the action plan generator 440.

The second controller 460 includes, for example, an acquirer 462, a speed controller 464, and a steering controller 466.

The acquirer 462 acquires information about the target trajectory (trajectory point) generated by the action plan generator 440 and stores it in a memory of the storage 480.

The speed controller 464 controls one or both of the traveling driving force output device 500 and the brake device 510 based on speed elements (for example, a target speed and a target acceleration) included in the target trajectory stored in the memory.

The steering controller 466 controls the steering device 520 according to the position element (for example, a curvature indicating the degree of curve of the target trajectory) included in the target trajectory stored in the memory.

The processing of the speed controller 464 and the steering controller 466 is realized by, for example, a combination of feedforward control and feedback control. As an example, the steering controller 466 executes a combination of feedforward control according to the curvature of the road in front of the host vehicle M and feedback control based on the deviation of the host vehicle M with respect to the target trajectory.

The traveling driving force output device 500 outputs a traveling driving force (torque) with which the vehicle travels to driving wheels. The traveling driving force output device 500 includes, for example, a combination of an internal combustion engine, an electric motor, a transmission, and the like, and a power electronic controller (ECU) that controls them. The power ECU controls the above configuration according to information input from the second controller 460 or information input from the driving operator 380.

The brake device 510 includes, for example, a brake caliper, a cylinder that transmits a hydraulic pressure to the brake caliper, an electric motor that generates a hydraulic pressure in the cylinder, and a brake ECU. The brake ECU controls the electric motor according to information input from the second controller 460 or information input from the driving operator 380 and outputs a brake torque according to the braking operation to wheels. The brake device 510 may include a mechanism that transmits a hydraulic pressure generated when the brake pedal included in the driving operator 380 is operated to the cylinder via a master cylinder as a backup. Here, the brake device 510 is not limited to the above-described configuration and may be an electronically controlled hydraulic brake device that controls an actuator according to information input from the second controller 460 and transmits a hydraulic pressure of the master cylinder to the cylinder.

The steering device 520 includes, for example, a steering ECU and an electric motor. The electric motor applies a force to, for example, a rack and pinion mechanism, and changes the direction of steered wheels. The steering ECU drives the electric motor according to information input from the second controller 460 or information input from the driving operator 380, and changes the direction of the steered wheels.

[Automatic Driving Based on Guidance Information]

Figure 18:
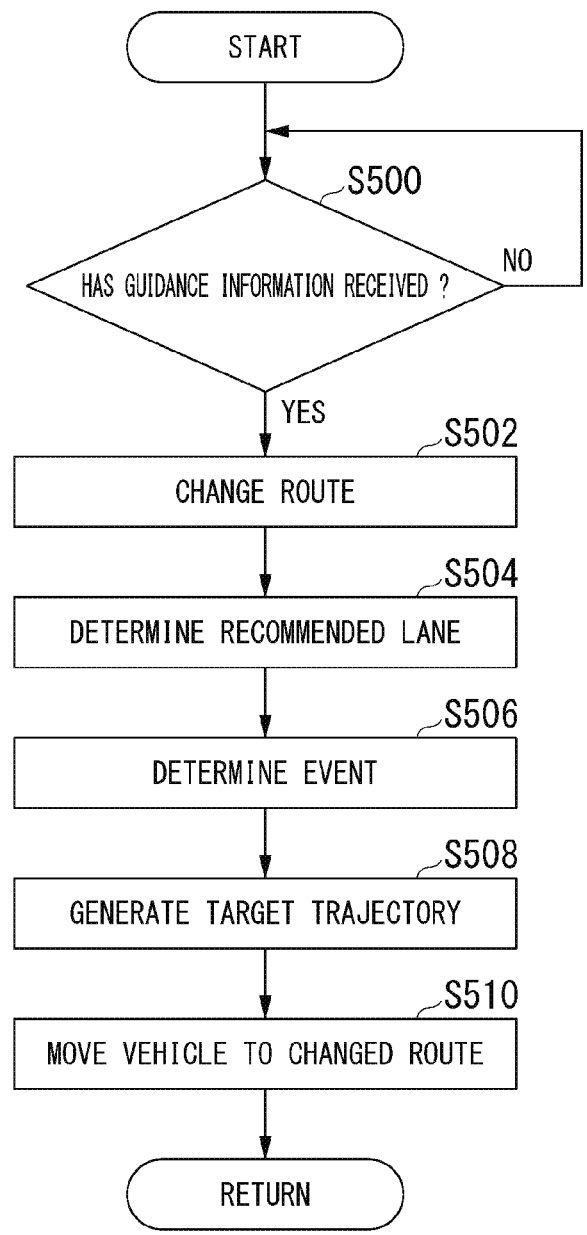
FIG. 18 is a flowchart showing a flow of a series of processes of the vehicle system according to the third embodiment.

An automatic driving based on guidance information will be described below with reference to a flowchart. FIG. 18 is a flowchart showing a flow of a series of processes of the vehicle system 2 according to the third embodiment. The process of this flowchart may be repeated at predetermined time intervals.

First, the guide device 100 waits until guidance information for prompting to change the route is received from the server device 200 (Step S500), and when guidance information for prompting to change the route is received from the server device 200, the guide device 100 changes the route to the destination to a route having few occurrence spots of the predetermined event or a low occurrence probability of the predetermined event according to the guidance information (Step S502).

Next, the MPU 360 determines a recommended lane from one or more lanes included in the route changed by the guide device 100 (Step S504).

Next, the action plan generator 440 determines an automatic driving event in the changed route on which a recommended lane is determined (Step S506), and generates a target trajectory according to the determined event (Step S508).

Next, the second controller 460 controls the traveling driving force output device 500, the brake device 510, and the steering device 520 based on the target trajectory generated by the action plan generator 440 in the process of S508, and thus moves the host vehicle M from the current route to a route having few occurrence spots of the predetermined event or a low occurrence probability of the predetermined event (Step S510). Thereby, the process of this flowchart ends.

According to the third embodiment described above, when guidance information for prompting to change the route is generated by the server device 200, since the automatic driving control device 400 moves the host vehicle M to a route to which change is prompted according to automatic driving, the vehicle M can be guided to a more appropriate route on which an unforeseen situation is less likely to be caused.

The embodiment described above can be represented as follows.

A vehicle control device including an output device which is provided in a first moving body and is configured to output information to the interior of the first moving body;

a storage in which a program is stored; and a processor, wherein, when the processor executes the program,
position information indicating an occurrence position of a predetermined event that occurred due to at least the feelings of an occupant in a moving body is acquired,
position information indicating a position of the first moving body is acquired, and
guidance information for providing guidance to the occupant in the first moving body regarding the fact that there is a possibility of the predetermined event occurring in the first moving body is output by the outputter based on the position information indicating the occurrence position of the predetermined event and the position information indicating the position of the first moving body.

While forms for implementing the present invention have been described above with reference to embodiments, the present invention is not limited to these embodiments, and various modifications and substitutions can be made without departing from the scope and spirit of the present invention.

What is claimed is:

1. A guidance system, comprising:
a display device which is provided in a first moving body and is configured to output information to an interior of the first moving body; and
a processor configured to:
acquire first position information indicating an occurrence position of a predetermined event that occurred due to at least the feelings of an occupant in a moving body, wherein the feelings of the occupant is determined based on voice data and image data associated with the occupant;
acquire second position information indicating a position of the first moving body; and
cause the display device to display guidance information for providing guidance to the occupant in the first moving body regarding the predetermined event occurring in the first moving body according to the first position information and the second position information.

2. The guidance system according to claim 1, wherein the processor is further configured to:
estimate the feelings of the occupant in the first moving body,
cause the display device to display the guidance information according to the first position information, the second position information, and the feelings of the occupant.

3. The guidance system according to claim 2,
wherein the display device is configured to display an image, and
wherein the processor is configured to cause the display to display a map on which the first position information is superimposed as the guidance information.

4. The guidance system according to claim 2, wherein the processor is further configured to:
acquire path information indicating a first route along which the first moving body is scheduled to travel, and
cause the display device to display information for prompting the occupant in the first moving body to change the first route to a second route on which the predetermined event is less likely to occur than on the first route according to the first route indicated by the path information, the first position information, and the feelings of the occupant as the guidance information.

5. The guidance system according to claim 2, wherein the processor is further configured to:
determine a first route along which the first moving body is scheduled to travel, and
change the first route to a second route on which the predetermined event is less likely to occur than on the first route according to the first route, the first position information, and the feelings of the occupant.

6. The guidance system according to claim 2, wherein the processor is further configured to:
control a speed and steering of the first moving body; and
acquire route information indicating a first route along which the first moving body is scheduled to travel in the future, and
move the first moving body from the first route to a second route on which the predetermined event is less likely to occur than on the first route according to the first route indicated by the route information, the first position information, and the feelings of the occupant.

7. The guidance system according to claim 2,
wherein, when the position of the first moving body indicated by the second position information is on a route along which the moving body has traveled before it reaches a spot at which the predetermined event has occurred, and the feelings of the occupant is included in a history of the feelings of the occupant in the moving body before it reaches the spot at which the predetermined event has occurred, the processor is further configured to cause the display device to display the guidance information.

8. The guidance system according to claim 2, the processor is further configured to:
acquire speed information indicating a speed of the first moving body,
wherein, when the position of the first moving body indicated by the second position information is on a route along which the moving body has traveled before it reaches a spot at which the predetermined event has occurred, and the feelings of the occupant is included in a history of the feelings of the occupant in the moving body before it reaches the spot at which the predetermined event has occurred, and additionally, the speed of the first moving body indicated by the speed information is included in a history of the speed of the moving body before it reaches a spot at which the predetermined event has occurred, the processor is further configured to cause the display device to display the guidance information.

9. The guidance system according to claim 2,
wherein, when the position of the first moving body indicated by the second position information is on a route along which the moving body has traveled before it reaches a spot at which the predetermined event has occurred, and the feelings of the occupant is included in a history of the feelings of the occupant in the moving body before it reaches the spot at which the predetermined event has occurred, and additionally whether when the feelings of the occupant is the same as whether when the predetermined event has occurred, the processor is further configured to cause the display device to display the guidance information.

10. The guidance system according to claim 2,
wherein, when the position of the first moving body indicated by the second position information is on a route along which the moving body has traveled before it reaches a spot at which the predetermined event has occurred, and the feelings of the occupant is included in a history of the feelings of the occupant in the moving body before it reaches the spot at which the predetermined event has occurred, and additionally, the time at which the feelings of the occupant is the same as the time at which the predetermined event has occurred, the processor is further configured to cause the display device to display the guidance information.

11. The guidance system according to claim 2,
wherein, when the first moving body is present in a predetermined area in which feelings of occupants in a plurality of moving bodies that have caused the predetermined event have a predetermined tendency representative of an inaction by the occupants in the plurality of the moving bodies to check a side mirror of the plurality of moving bodies, and the feelings of the occupant in the first moving body has the predetermined tendency, the processor is further configured to cause the display device to display the guidance information.

12. The guidance system according to claim 1,
wherein the guidance information includes information for guiding the occupant in the first moving body to change the route of the first moving body or information for prompting to change feelings.

13. A guidance system, comprising:
a display device which is provided in a first moving body and is configured to output information to an interior of the first moving body; and
a processor configured to:
acquire position information indicating a position of the first moving body;
estimate the feelings of an occupant in the first moving body, wherein the feelings of the occupant is determined based on voice data and image data associated with the occupant; and
cause the display device to display guidance information for providing guidance to the occupant in the first moving body regarding the predetermined event occurring in the first moving body according to output results of a model which is learned to predict that a predetermined event will occur when information including a position of a moving body and the feelings of the occupant in the moving body is input, in which information including a position of the first moving body indicated by the first position information and the feelings of the occupant in the first moving body is input to the model.

14. A guidance method causing a computer mounted in a first moving body including a display device configured to display information to:
acquire position information indicating an occurrence position of a predetermined event that occurred due to at least the feelings of an occupant in a moving body, wherein the feelings of the occupant is determined based on voice data and image data associated with the occupant;
acquire position information indicating a position of the first moving body; and
cause the display device to display guidance information for providing guidance to the occupant in the first moving body regarding the predetermined event occurring in the first moving body according to the position information indicating the occurrence position of the predetermined event and the position information indicating the position of the first moving body.

15. A computer-readable storage medium storing a program causing a computer mounted in a first moving body including a display device configured to display information to execute:
acquiring position information indicating an occurrence position of a predetermined event that occurred due to at least the feelings of an occupant in a moving body, wherein the feelings of the occupant is determined based on voice data and image data associated with the occupant;
acquiring position information indicating a position of the first moving body; and
causing the display device to display guidance information for providing guidance to the occupant in the first moving body regarding the predetermined event occurring in the first moving body according to the position information indicating the occurrence position of the predetermined event and the position information indicating the position of the first moving body.

* * * * *